(12) United States Patent
Lester et al.

(10) Patent No.: US 11,485,699 B2
(45) Date of Patent: Nov. 1, 2022

(54) (METH)ACRYLIC OLIGOMERS

(71) Applicant: Synthomer Adhesive Technologies LLC, Beachwood, OH (US)

(72) Inventors: Christopher Lee Lester, Danville, VA (US); Sarah Exley Goetz, Kingsport, TN (US); Timothy Harold Blayney, Piney Flats, TN (US); Gabrielle Rose Ashley, Kingsport, TN (US); Mark Stanley Pavlin, Kingsport, TN (US); Douglas Grant Atkins, Gray, TN (US); Zhufang Liu, Kingsport, TN (US)

(73) Assignee: Synthomer Adhesive Technologies LLC, Beachwood, OH (US)

( * ) Notice: Subject to any disclaimer, the term of this patent is extended or adjusted under 35 U.S.C. 154(b) by 0 days.

(21) Appl. No.: 16/314,966

(22) PCT Filed: Jul. 6, 2017

(86) PCT No.: PCT/US2017/040924
§ 371 (c)(1),
(2) Date: Jan. 3, 2019

(87) PCT Pub. No.: WO2018/009683
PCT Pub. Date: Jan. 11, 2018

(65) Prior Publication Data
US 2019/0308924 A1    Oct. 10, 2019

Related U.S. Application Data

(60) Provisional application No. 62/358,693, filed on Jul. 6, 2016.

(51) Int. Cl.
| | | |
|---|---|---|
| *C07C 67/465* | (2006.01) | |
| *C09J 133/06* | (2006.01) | |
| *C07C 69/54* | (2006.01) | |
| *C07C 67/00* | (2006.01) | |
| *C09J 133/08* | (2006.01) | |
| *C08F 120/14* | (2006.01) | |
| *C08F 120/18* | (2006.01) | |
| *C08F 120/20* | (2006.01) | |
| *C08F 2/38* | (2006.01) | |
| *C08F 8/04* | (2006.01) | |
| *C08F 220/18* | (2006.01) | |

(52) U.S. Cl.
CPC ............ *C07C 67/00* (2013.01); *C07C 67/465* (2013.01); *C08F 2/38* (2013.01); *C08F 8/04* (2013.01); *C08F 120/14* (2013.01); *C08F 120/18* (2013.01); *C08F 120/20* (2013.01); *C09J 133/06* (2013.01); *C09J 133/08* (2013.01); *C07C 69/54* (2013.01); *C08F 220/1808* (2020.02)

(58) Field of Classification Search
CPC ................ C08F 220/06; C07C 69/54
USPC ......................................................... 525/271
See application file for complete search history.

(56) References Cited

U.S. PATENT DOCUMENTS

| | | |
|---|---|---|
| 2,925,174 A | 2/1960 | Stow |
| 2,963,387 A | 12/1960 | Herr et al. |
| 3,445,263 A | 5/1969 | Alexander |
| 3,867,481 A | 2/1975 | Whang |
| 4,056,559 A | 11/1977 | Lewis et al. |
| 4,223,067 A | 9/1980 | Levens |
| 4,694,054 A | 9/1987 | Janowicz |
| 4,726,982 A | 2/1988 | Traynor et al. |
| 4,912,169 A | 3/1990 | Whitmire et al. |
| 5,006,582 A | 4/1991 | Mancinelli |
| 5,028,677 A | 7/1991 | Janowicz |
| 5,164,441 A | 11/1992 | Yang |
| 5,439,748 A | 8/1995 | Nakamura et al. |
| 5,851,663 A | 12/1998 | Parsons et al. |

(Continued)

FOREIGN PATENT DOCUMENTS

| | | |
|---|---|---|
| CN | 104017486 A | 9/2014 |
| CN | 103432623 B | 4/2015 |

(Continued)

OTHER PUBLICATIONS

Notification of Transmittal of the International Search Report and the Written Opinion of the International Searching Authority, or the Declaration received in International Application No. PCT/US2017/040924 dated Sep. 8, 2017.

(Continued)

*Primary Examiner* — Ana Z Muresan
(74) *Attorney, Agent, or Firm* — Hovey Williams LLP; Kameron D. Kelly

(57) ABSTRACT

The invention provides (meth)acrylic oligomers prepared from C1-C20 alkyl and C5-C20 cycloalkyl (meth)acrylates, wherein said oligomers have a Mn of about 300 g/mole to about 3,000 g/mole; a Mw of about 700 g/mole to about 6,000 g/mole; a Mz of about 900 g/mole to about 10,000 g/mole. The oligomers may have a Yellowness Index, according to ASTM E313 of less than 2. The oligomers of the invention are useful as tackifiers in adhesive compositions, but also are believed to be useful also in general polymer modification as plasticizers, leveling agents, viscosity reducers (i.e., rheology modifiers), and for increasing solids content in solvent-borne applications of all types with little detrimental impact on viscosity. The invention also provides adhesive compositions and laminate articles coated on at least one side with the adhesive compositions of the invention.

17 Claims, 6 Drawing Sheets

(56) References Cited

U.S. PATENT DOCUMENTS

| | | |
|---|---|---|
| 5,930,442 A | 7/1999 | Abramowicz et al. |
| 6,022,927 A | 2/2000 | Decker et al. |
| 6,024,948 A | 2/2000 | Samain et al. |
| 6,025,030 A | 2/2000 | Decker et al. |
| 6,103,316 A | 8/2000 | Tran et al. |
| 6,300,407 B1 | 10/2001 | Machleder et al. |
| 6,306,546 B1 | 10/2001 | LaFleur et al. |
| 6,353,068 B1 | 3/2002 | Dietz et al. |
| 6,388,026 B1 | 5/2002 | Campbell et al. |
| 6,451,141 B1 | 9/2002 | Krobb et al. |
| 6,503,975 B1 | 1/2003 | Huybrechts |
| 6,511,744 B2 | 1/2003 | Centner et al. |
| 6,521,732 B2 | 2/2003 | Perez et al. |
| 6,638,602 B2 | 10/2003 | Itada et al. |
| 6,642,298 B2 | 11/2003 | Foreman et al. |
| 6,656,410 B2 | 12/2003 | Hull et al. |
| 6,657,011 B2 | 12/2003 | Lau et al. |
| 6,720,375 B2 | 4/2004 | Suzuki et al. |
| 6,780,897 B1 | 8/2004 | Blum et al. |
| 6,783,850 B2 | 8/2004 | Takizawa et al. |
| 6,844,396 B2 | 1/2005 | Sugaya et al. |
| 6,855,796 B2 | 2/2005 | Lachowicz et al. |
| 6,939,911 B2 | 9/2005 | Tosaki et al. |
| 7,071,264 B2 | 7/2006 | Darling et al. |
| 7,105,207 B2 | 9/2006 | Warmkessel et al. |
| 7,112,626 B1 | 9/2006 | Fickeisen et al. |
| 7,217,758 B2 | 5/2007 | Buckmann et al. |
| 7,262,242 B2 | 8/2007 | Gielens et al. |
| 7,297,743 B2 | 11/2007 | Kanamori et al. |
| 7,300,996 B2 | 11/2007 | Hoffmann et al. |
| 7,365,105 B2 | 4/2008 | Kiefer-Liptak |
| 7,378,478 B2 | 5/2008 | Eu et al. |
| 7,420,013 B2 | 9/2008 | Riegel et al. |
| 7,452,931 B2 | 11/2008 | Mae et al. |
| 7,491,759 B2 | 2/2009 | Wilke et al. |
| 7,569,272 B2 | 8/2009 | Ohrui et al. |
| 7,622,168 B2 | 11/2009 | Ogasawara et al. |
| 7,638,579 B2 | 12/2009 | Finch et al. |
| 7,687,576 B2 | 3/2010 | Klein et al. |
| 7,700,703 B2 | 4/2010 | Hughes et al. |
| 7,723,466 B2 | 5/2010 | Theelen et al. |
| 7,772,318 B2 | 8/2010 | Fasano et al. |
| 7,816,434 B2 | 10/2010 | Hackbarth et al. |
| 7,829,606 B2 | 11/2010 | Lu et al. |
| 7,829,615 B2 | 11/2010 | Slark |
| 7,923,513 B2 | 4/2011 | Killilea et al. |
| 7,935,762 B2 | 5/2011 | Husemann et al. |
| 8,038,832 B2 | 10/2011 | Tanaka |
| 8,039,541 B2 | 10/2011 | Mae |
| 8,043,424 B2 | 10/2011 | Thiel et al. |
| 8,053,540 B2 | 11/2011 | Eu et al. |
| 8,088,864 B2 | 1/2012 | Kishioka |
| 8,263,706 B2 | 9/2012 | Fraser et al. |
| 8,299,182 B2 | 10/2012 | Inokuchi et al. |
| 8,318,852 B2 | 11/2012 | Kim et al. |
| 8,362,131 B2 | 1/2013 | Gane et al. |
| 8,404,788 B2 | 3/2013 | Matyjaszewski et al. |
| 8,519,043 B2 | 8/2013 | Hartig et al. |
| 8,530,362 B2 | 9/2013 | Nungesser et al. |
| 8,592,525 B2 | 11/2013 | Schultes et al. |
| 8,623,961 B2 | 1/2014 | Akiyama et al. |
| 8,652,511 B2 | 2/2014 | Cottrell et al. |
| 8,710,139 B2 | 4/2014 | Shigetomi et al. |
| 8,722,829 B2 | 5/2014 | Schumacher et al. |
| 8,748,523 B2 | 6/2014 | Gane et al. |
| 8,764,933 B2 | 7/2014 | Takatsu et al. |
| 8,828,539 B2 | 9/2014 | Hirose et al. |
| 8,877,883 B2 | 11/2014 | Kim et al. |
| 8,883,926 B2 | 11/2014 | Okamoto et al. |
| 9,011,995 B2 | 4/2015 | Park et al. |
| 9,102,767 B2 | 8/2015 | Dolmazon et al. |
| 9,120,934 B2 | 9/2015 | Tsai et al. |
| 9,221,992 B2 | 12/2015 | Bohling et al. |
| 9,371,474 B2 | 6/2016 | Schall et al. |
| 9,487,679 B2 | 11/2016 | Ogata et al. |
| 2006/0173120 A1 | 8/2006 | Baumgart et al. |
| 2008/0194759 A1 | 8/2008 | Casper |
| 2009/0202818 A1 | 8/2009 | Kasahara et al. |
| 2010/0036042 A1 | 2/2010 | Krueger et al. |
| 2011/0070434 A1 | 3/2011 | Hirose et al. |
| 2011/0250433 A1 | 10/2011 | Inokuchi et al. |
| 2011/0250446 A1 | 10/2011 | Higuchi et al. |
| 2012/0083572 A1* | 4/2012 | Klots .................. C09D 125/14 524/576 |
| 2013/0005911 A1 | 1/2013 | Okamoto et al. |
| 2013/0011672 A1 | 1/2013 | Okamoto et al. |
| 2013/0078463 A1 | 3/2013 | Okamoto et al. |
| 2013/0131223 A1 | 5/2013 | Bouguettaya et al. |
| 2013/0177758 A1 | 7/2013 | Shigetomi et al. |
| 2014/0037951 A1 | 2/2014 | Shigetomi et al. |
| 2014/0147668 A1 | 5/2014 | Yamagata et al. |
| 2015/0148431 A1 | 5/2015 | Cottrell et al. |
| 2015/0307751 A1 | 10/2015 | Eckhardt et al. |

FOREIGN PATENT DOCUMENTS

| | | |
|---|---|---|
| EP | 0 312 228 A1 | 4/1989 |
| EP | 0 801 661 B2 | 10/1997 |
| EP | 0 940 433 B1 | 9/1999 |
| EP | 0 941 261 B1 | 9/1999 |
| EP | 1 002 847 B1 | 5/2000 |
| EP | 1 005 514 B1 | 6/2000 |
| EP | 1 058 708 B1 | 12/2000 |
| EP | 1 117 622 B1 | 7/2001 |
| EP | 1 317 518 B1 | 6/2003 |
| EP | 1 649 077 B1 | 4/2006 |
| EP | 1 664 134 B1 | 6/2006 |
| EP | 1 686 160 B1 | 8/2006 |
| EP | 1731 572 B1 | 12/2006 |
| EP | 1739 128 B1 | 1/2007 |
| EP | 1 842 888 B1 | 10/2007 |
| EP | 1 877 486 B1 | 1/2008 |
| EP | 1 969 078 B1 | 9/2008 |
| EP | 2 028 202 B1 | 2/2009 |
| EP | 2 100 933 A1 | 9/2009 |
| EP | 2 139 967 B1 | 1/2010 |
| EP | 2 141 181 B1 | 1/2010 |
| EP | 2 141 210 A1 | 1/2010 |
| EP | 2 385 089 A1 | 11/2011 |
| EP | 2 385 090 B1 | 11/2011 |
| EP | 2 788 425 B1 | 10/2014 |
| JP | 08027450 A | 1/1996 |
| JP | 2001049200 A | 2/2001 |
| JP | 2006096958 A | 4/2006 |
| WO | WO 1992 001748 A1 | 2/1992 |
| WO | WO 2003 016413 A1 | 2/2003 |
| WO | WO 2008 038956 A1 | 4/2008 |
| WO | WO 2009 009071 A1 | 1/2009 |
| WO | WO 2011 073221 A3 | 8/2011 |
| WO | WO 2011 073341 A3 | 10/2011 |
| WO | WO 2013 013590 A1 | 1/2013 |
| WO | WO 2013 167537 A1 | 11/2013 |

OTHER PUBLICATIONS

Leong, Yub Choong et al.; "The Viscoelastic Properties of Natural Rubber Pressure-Sensitive Adhesive Using Acrylic Resin as a Tackifier"; Journal of Applied Polymer Science, vol. 88; 2003; pp. 2118-2123.

* cited by examiner

(METH)ACRYLIC OLIGOMERS

CROSS-REFERENCE TO RELATED APPLICATION

This application is a national stage filing under 35 USC § 371 of International Application Number PCT/US2017/040924, filed on Jul. 6, 2017, which claims the benefit of the filing date to U.S. Provisional Application No. 62/358,693 filed on Jul. 6, 2016, the entire disclosures of which are incorporated by reference herein.

FIELD OF THE INVENTION

This invention relates to the field of adhesives. In particular, it relates to oligomeric (meth)acrylic materials useful as tackifiers in adhesive, sealant, and other elastomeric compositions.

BACKGROUND

There are limited options for tackifying more polar adhesive systems. Also, there are few or no tackifiers that are water white and offer excellent oxidative, thermal and UV resistance. Benefits of tackifying resins for adhesives are as follows: improved solids content or lower melt viscosities, which lead to processing benefits like faster line speeds, defect free coatings, and the ability to coat thick films. Another benefit is improved adhesion in general and, specifically, improved adhesion to low surface energy plastics which polar systems are known to often have difficulties with due to their more polar nature relative to other elastomers. In general, natural product derived rosin based tackifiers, terpene phenolics, and in some systems polyterpene resins have broad compatibility and do improve adhesion. However, these materials do not always provide the oxidative, thermal, and UV stability that the base polymer provides. Furthermore, there are inherent limits on the existing tackifying resins composition (polarity) and types of chemical functionalities. Additionally, the stabilized and hydrogenated versions of current resins can be expensive, limiting their use. Resins which are prepared from C5/C9, partially hydrogenated C9 or partially hydrogenated pure monomers have some compatibility with polar adhesive systems, but their residual unsaturation and aromaticity detracts from the long-term stability of the formulated product. Fully hydrogenated hydrocarbon resins of any feedstock are incompatible with most polar adhesive systems and again, like the rosin products, hydrogenation and stabilization add significant cost to the product.

This invention, as described below, provides certain low molecular weight (meth)acrylic copolymers to be utilized as tackifying resins for more polar adhesive systems. Specifically, this work has been concentrated on the modification of (meth)acrylic thermoplastics and thermosets useful as high performance pressure sensitive adhesives. These copolymers are synthesized utilizing free-radical solution polymerization. One significant challenge to overcome is making the copolymers low enough in molecular weight so they can function as a tackifier and have broad based compatibility with a wide range of adhesive base polymers. This is difficult due to the propensity of these types of monomers and polymerization processes to produce high molecular weight products. Appropriate process conditions, choice of solvents, initiator, and possibly a chain transfer agent allow for the ability to achieve molecular weights of <10,000 g/mole (number average molecular weight) but do not eliminate high molecular weight fractions that are part of these polydisperse systems. Catalytic chain transfer agents such as various cobalt compounds have been reported to afford molecular weights as low as 300 g/mole (number average molecular weight) with the elimination of any high molecular weight fraction.

SUMMARY

The invention provides (meth)acrylic oligomers prepared from $C_1$-$C_{20}$ alkyl and $C_5$-$C_{20}$ cycloalkyl (meth)acrylates, wherein said oligomers have a number average molecular weight ($M_n$) of about 300 g/mole to about 3,000 g/mole; a weight average molecular weight ($M_w$) of about 700 g/mole to about 6,000 g/mole; a z-average molecular weight ($M_z$) of about 900 g/mole to about 10,000 g/mole; and wherein the Yellowness Index, according to ASTM E313 is less than 2. The oligomers of the invention are useful as tackifiers in adhesive compositions, but are also believed to be useful in general polymer modification as plasticizers, leveling agents, viscosity reducers (i.e., rheology modifiers), and for increasing solids content in solvent-borne applications of all types with little detrimental impact on viscosity. Accordingly, the invention also provides adhesive compositions and laminate articles coated on at least one side with the adhesive compositions of the invention.

DETAILED DESCRIPTION

Figure 1:
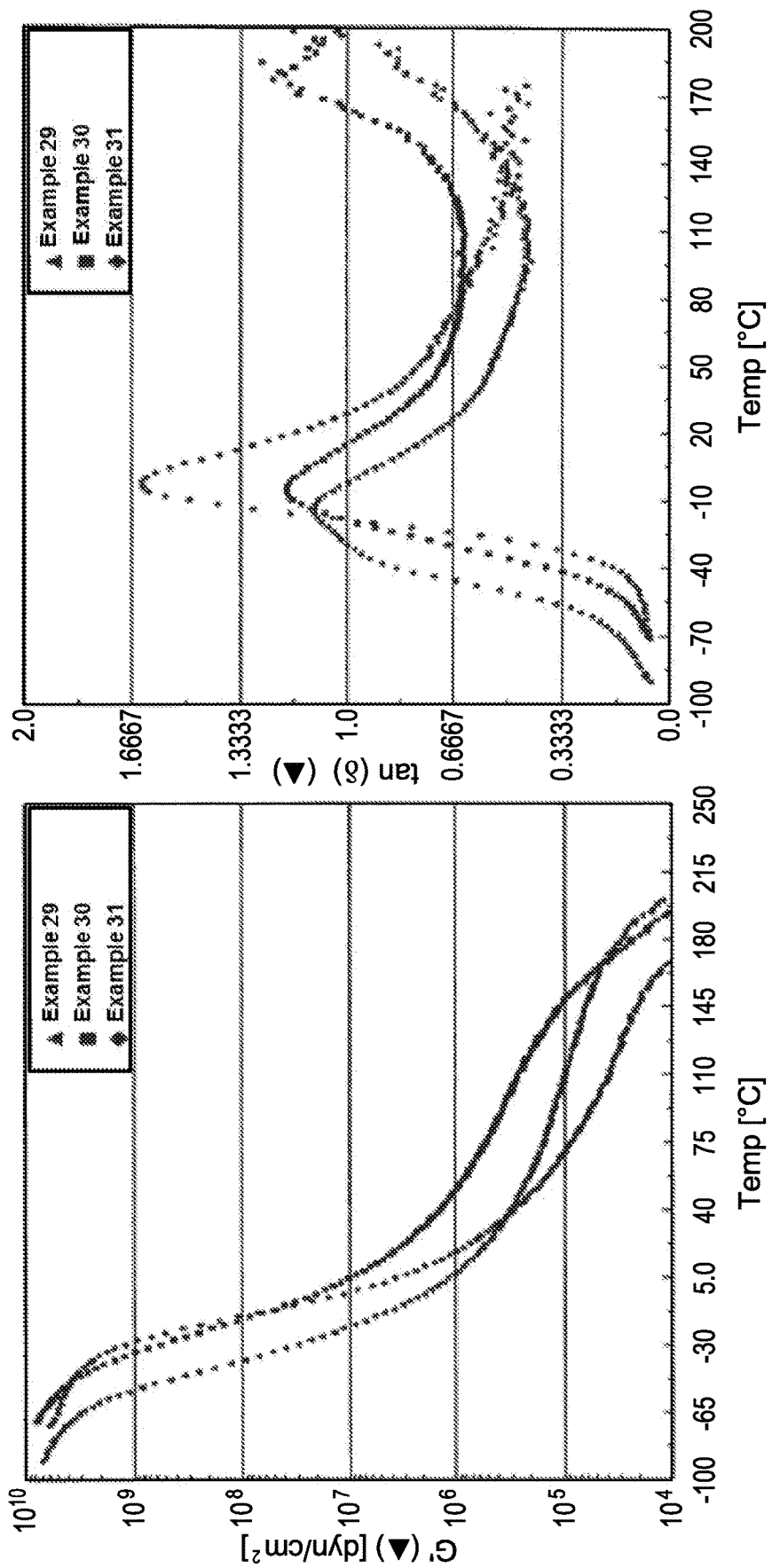
FIG. 1 is a plot of storage modulus and tan δ as a function of temperature of the model PSA 1 and the model PSA 1 blended with the comparative example and Example 2 at 50% by weight solid polymer.

In one embodiment, the invention provides acrylic oligomers prepared from $C_1$-$C_{20}$ alkyl and $C_5$-$C_{20}$ cycloalkyl (meth)acrylates, wherein said oligomers have a $M_n$ molecular weight of about 300 g/mole to about 3,000 g/mole; a $M_w$ molecular weight of about 700 g/mole to about 6,000 g/mole; a $M_z$ molecular weight of about 900 g/mole to about 10,000 g/mole. The oligomers may have a Yellowness Index, according to ASTM E313, of less than 2. These oligomers may be homopolymeric or copolymeric oligomers. The oligomers may be hydrogenated and have a residual olefin content, measured by $^1$H NMR, of less than 3.5 weight percent.

In other embodiments, the oligomers may have a $M_n$ molecular weight of at least about 300, at least about 400, at least about 500, at least about 600, at least about 700, at least about 800 g/mole and/or not more than about 3000, not more than about 2500, not more than about 2100, not more than about 2000, not more than about 1900, not more than about 1800, or not more than about 1700 g/mole or the $M_n$ molecular weight can be in the range of from about 300 to about 3000, about 400 to about 2,100 g/mole, about 500 to about 2,000 g/mole, about 600 to about 1,900 g/mole, about 700 to about 2500 g/mole, about 700 to about 1800 g/mole, or about 800 to about 1,700 g/mole.

In other embodiments, the oligomers may have a $M_w$ molecular weight of at least about 700, at least about 800, at least about 900, at least about 1000, or at least about 1100 g/mole and/or not more than about 6000, not more than about 5500, not more than about 5000, not more than about 4500, not more than about 4000, not more than about 3700, not more than about 3600, not more than about 3500, not more than about 3400, not more than about 3300 g/mole. The oligomer may have an $M_n$ molecular weight in the range of from about of 700 to about 6000 g/mole, about 800 to about 3,600 g/mole, about 900 to about 3,500 g/mole, about 1000 to about 3,400 g/mole, or about 1100 to about 3,300 g/mole.

In other embodiments, the oligomers may have a $M_z$ molecular weight of at least about 900, at least about 1000, at least about 1200, at least about 1400, at least about 1500, at least about 2000, at least about 2500, at least about 3500, at least about 4000, at least about 4500, or at least about 5000 g/mole. Alternatively, or in addition, the oligomers can have a $M_z$ molecular weight of not more than about 10,000, not more than about 9500, not more than about 9000, not more than about 8500, not more than about 8000, not more than about 7500, not more than about 7000, not more than about 6500, not more than about 6000, not more than about 5600, not more than about 5500, not more than about 5000, not more than about 4500, not more than about 4000, not more than about 3500, not more than about 3000, or not more than about 2500.

The oligomers may have $M_z$ molecular weight in the range of from 900 to 10,000 g/mole, from about 1000 to about 9000 g/mole, from about 1000 to about 6000 g/mole, about 1000 to about 3000 g/mole, from about 1200 to about 10,000, from about 1400 to about 6000 g/mole, from about 1500 to about 5600, from about 2,000 to about 5,600 g/mole, from about 1500 to about 3500 g/mole, from about 3500 to about 5000 g/mole, from about 4500 to about 6000 g/mole, from about 1500 to about 2500 g/mole, from about 2500 to about 3500 g/mole, from about 3500 to about 4500 g/mole, or from about 5000 to about 6000 g/mole.

In some embodiments, the oligomers can have a polydispersity of less than 3.5. Polydispersity is calculated by dividing the $M_w$ molecular weight by the $M_n$ molecular weight ($M_w/M_n$). The oligomers described herein may have a polydispersity of less than 3.25, less than 3.0, less than 2.75 less than 2.5, less than 2.25, less than 2.0, or less than 1.75. The oligomers of the present invention may be substantially devoid (e.g., less than 5 weight percent) of high molecular weight fractions in order to be practically useful as tackifiers.

The acrylic oligomers of the invention can be prepared from monomers selected from $C_1$-$C_{20}$ alkyl and $C_5$-$C_{20}$ cycloalkyl acrylates, $C_1$-$C_{20}$ alkyl and $C_5$-$C_{20}$ cycloalkyl methacrylates, free-radical polymerizable olefinic acids, such as methacrylic acid (MAA), and optionally other ethylenically unsaturated monomers. In some cases, the acrylic oligomers can be formed from monomers selected from $C_1$-$C_{12}$ alkyl and cycloalkyl (meth)acrylates, $C_2$-$C_{10}$ alkyl and cycloalkyl (meth)acrylates, or $C_2$-$C_5$ alkyl (meth)acrylates. The cycloalkyl (meth)acrylates may include mono-cyclic, bi-cyclic, or multi-cyclic alkyl groups.

Examples of suitable $C_1$-$C_{20}$ alkyl and $C_5$-$C_{20}$ cycloalkyl acrylates include methyl acrylate (MA), ethyl acrylate, n-propyl acrylate, isopropyl acrylate, n-butyl acrylate, isobutyl acrylate, tert-butyl acrylate, isobornyl acrylate, pentyl acrylate, hexyl acrylate, octyl acrylate iso-octyl acrylate, nonyl acrylate, lauryl acrylate, stearyl acrylate, eicosyl acrylate, 2-ethylhexyl acrylate, cyclohexyl acrylate cycloheptyl acrylate, 4-hydroxybutyl acrylate (HBA) and the like and mixtures thereof. Examples of $C_1$-$C_{20}$ alkyl and $C_5$-$C_{20}$ cycloalkyl methacrylates include methyl methacrylate (MMA), n-butyl methacrylate, tert-butyl methacrylate (tBMA), isobutyl methacrylate (iBMA), pentyl methacrylate, hexyl methacrylate, cyclohexyl methacrylate (CHMA), 2-ethylhexyl methacrylate (EHMA), isobornyl methacrylate (IBOMA), heptyl methacrylate, cycloheptyl methacrylate, octyl methacrylate, iso-octyl methacrylate, nonyl methacrylate, decyl methacrylate, lauryl methacrylate, eicosyl methacrylate, ethylene glycol phenyl ether methacrylate (EPhEMA), benzyl methacrylate (BzMA), 2-hydroxyethyl methacrylate (HEMA) and the like and mixtures thereof. In some cases, the $C_1$-$C_{20}$ alkyl and $C_5$-$C_{20}$ cycloalkyl may be selected from the group consisting of cyclohexyl, methyl, t-butyl, isobutyl, norbornyl, dicyclopentadienyl, and isobornyl.

In one embodiment, the invention provides (meth)acrylic oligomers prepared from one or more of the monomers selected from the group consisting of methyl (meth)acrylate, t-butyl (meth)acrylate, isobutyl (meth)acrylate, isobornyl (meth)acrylate. Example structures for several of these monomers is shown below.

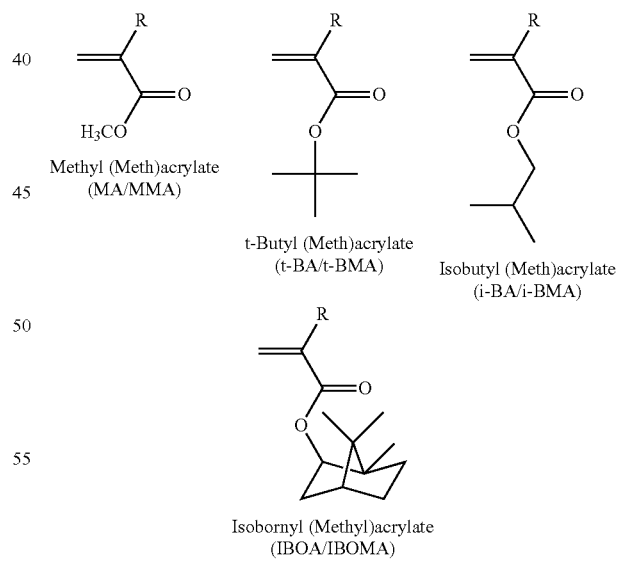

Methyl (Meth)acrylate (MA/MMA)

t-Butyl (Meth)acrylate (t-BA/t-BMA)

Isobutyl (Meth)acrylate (i-BA/i-BMA)

Isobornyl (Methyl)acrylate (IBOA/IBOMA)

Several properties of (meth)acrylic monomers suitable for use are summarized in Table 1, below. As used herein, the term "(meth)acrylate" (or "(meth)acrylic") refers to an acrylate or a methacrylate (or acrylic or methacrylic), while the term "acrylate" (or "acrylic") refers only to the acrylate (or acrylic) and the term "methacrylate" (or "methacrylic") refers only to the methacrylate (or methacrylic).

TABLE 1

Properties of Several (Meth)acrylic Monomers

| Monomer | $T_g$ °C. | Fedor's Solubility Parameter | |
|---|---|---|---|
| | | $\delta$ (cal/mole)$^{0.5}$ | Apparent $\delta$ (cal/mole)$^{0.5}$ |
| MA | 10 | 10.56 | 10.56 |
| MMA | 105 | 9.93 | 9.93 |
| t-BA | 50 | 9.36 | 9.24 |
| t-BMA | 105 | 9.07 | 9 |
| i-BA | −24 | 9.57 | 9.57 |
| i-BMA | 53 | 9.27 | 9.27 |
| IBOA | 94 | 9.71 | 8.82 |
| IBOMA | 170 | 9.5 | 8.7 |

In some embodiments, the (meth)acrylic oligomers of the present invention may comprise homopolymeric oligomers. As used herein, the term "homopolymeric" refers to an oligomeric or polymeric compound including more than 92 weight percent of residues of a single monomeric component, based on the total weight of the oligomer or polymer. In some cases, homopolymeric oligomers can include at least about 93, at least about 95, at least about 97, at least about 99, or at least about 99.5 weight percent of a single monomeric component, based on the total weight of the oligomer. Thus, homopolymeric oligomers as described herein may include not more than about 8, not more than about 7, not more than about 5, not more than about 3, not more than about 1 or not more than about 0.5 weight percent of residues of one or more co-monomers.

The (meth)acrylic oligomers of the invention can be prepared by known polymerization processes such as emulsion, suspension, solution or bulk polymerization. It is preferred to prepare via solution or bulk polymerization in absence of surface active agents or other ionic impurities common to suspension or emulsion polymerization. It is most preferable to utilize a very low concentration of free-radical initiator (e.g., AIBN) and in the presence of a catalytic chain transfer agent without the use of a conventional chain transfer agent such as a mercaptan. In some embodiments, the total amount of conventional chain transfer agents, such as mercaptan or other thiol-group containing compounds, may be not more than about 0.50, not more than about 0.30, not more than about 0.25, not more than about 0.10, or not more than about 0.05 weight percent, based on the total weight of the polymerization reaction medium. As a result, the oligomers may include not more than about 0.10, not more than about 0.05, or not more than about 0.01 weight percent of residues of any mercaptan or thiol-containing compounds.

Specifically, the (meth)acrylate oligomers of the invention may be prepared by solution polymerization at concentrations of 40 through 99 wt % solids. In some embodiments, the polymerization may be performed at concentrations of at least about 45, at least about 50, at least about 55, at least about 60, or at least about 65 wt % solids and/or not more than about 95, not more than about 90, not more than about 85, not more than about 80, or not more than about 75 wt % solids. The reaction may be held under reflux; however, if ethyl acetate is being used as the solvent, the reaction temperatures may be in the range of from about 70 to about 100° C. In some embodiments, the reaction temperature may be at least about 70, at least about 75, or at least about 80° C. and/or not more than about 100, not more than about 95, not more than about 90, or not more than about 85° C. The reaction may be conducted under ambient conditions.

In some embodiments, a range of 0.05 mg of catalytic chain transfer agent per 1 kg of monomer through 1 g of catalytic chain transfer agent per 1 kg of monomer may be used, or the amount of catalytic chain transfer agent may be at least about 0.10, at least about 0.50, at least about 1, at least about 5, at least about 10 mg per 1 kg of monomer and/or not more than about 900, not more than about 800, not more than about 700, not more than about 600, not more than about 500, not more than about 400, not more than about 300, or not more than about 250 mg of chain transfer agent per 1 kg of monomer. Initiator concentrations in the range of 1 g of initiator per 1000 g of monomer to 10 g of initiator per 1000 g of monomer may be used. In some cases, the amount of initiator present may be at least about 2, at least about 4, at least about 5 g of initiator per 1000 g of monomer and/or not more than about 9, not more than about 8, or not more than about 7 g of initiator per 1000 g of monomer.

Feed rates of 0.1 g/min through 10 g/min may be used. In some cases, the feed rate into the reaction zone may be at least about 0.1, at least about 0.2, at least about 0.3, at least about 0.4, at least about 0.5, at least about 0.75, at least about 0.90, at least about 1, at least about 1.2, at least about 1.5, at least about 1.75, or at least about 1.9 g/min and/or not more than about 10, not more than about 9, not more than about 8, not more than about 7, not more than about 6, not more than about 5, not more than about 4, not more than about 3, not more than about 2.5, not more than about 2, not more than about 1.5, or not more than about 1 g/min. In some cases, the feed rate may be changed (e.g., increased or decreased) at one or more points during the reaction.

Hold times of 30 min through 2 hours may be used. In some embodiments, the hold times may be at least about 15, at least about 30, at least about 45 minutes, or at least about 55 minutes and/or not more than about 2, not more than about 1.75 hours, not more than about 1.5 hours, not more than about 1 hour, or not more than about 45 minutes. Depending on the reaction conditions, there may also be one or more, or two or more different hold times that each fall within one or more of the ranges above.

The resulting oligomers can be hydrogenated to provide partially or fully hydrogenated oligomers. Hydrogenation was found advantageous in reducing the color of the oligomer, as measured by the Yellowness Index (Y.I.) and the residual, especially end-group, unsaturation, as measured by proton nuclear magnetic resonance spectroscopy ($^1$H NMR). In some cases, the oligomers may have a Yellowness Index of less than 3, less than 2.5, less than 2, less than 1.75, less than 1.5, less than 1, or less than 0.75, measured according to ASTM E-313.

When performed, the hydrogenation of the (meth)acrylic oligomer can be carried out in a batch stirred tank reactor, or a continuously stirred tank reactor, or a tubular reactor, at temperature from 50 to 200° C., pressure from 50 psig to 1500 psig, and contact time from 0.06 to 4 hours, or even up to 6 hours. In some embodiments, the hydrogenation reaction temperature can be at least about 75, at least about 85, at least about 95, at least about 105, at least about 115° C. and/or not more than about 190, not more than about 180, not more than about 170, not more than about 160, not more than about 150, not more than about 140, or not more than about 130° C., and the pressure can be at least about 100, at least about 200, at least about 300, at least about 400, at least about 500, at least about 600, at least about 700, at least about 800, or at least about 900 psig and/or not more than about 1400, not more than about 1300, not more than about 1200, or not more than about 1100 psig. In some embodiments, the contact time of the hydrogenation reaction can be at least about 0.1, at least about 0.5, at least about 1, at least about 1.5, at least about 2, at least about 2.5, at least about 3, or at least about 3.5 hours and/or not more than about 6, not more than about 5.5, not more than about 5, or not more than about 4.5 hours.

The hydrogenation catalyst is chosen from Group VIII metals such as palladium (Pd), platinum (Pt), and nickel (Ni), which can be in a form of mono-metallic, or bi-metallic, or tri-metallic, with catalyst support such as metal oxides (e.g., alumina, silica), carbon, carbide, nitride, and zeolite. Sponge-type metal catalysts such as Raney® Ni can be also used in the hydrogenation. The catalyst may be pre-activated by treatment with hydrogen under pressure prior to use or used without special pre-treatment. The preferred catalyst is supported Pd.

The hydrogenation reaction can be carried out in any non-olefinic organic solvent as long as it can dissolve the (meth)acrylate oligomers. The concentration of the oligomers varies from 10 wt % to 60 wt %. In one embodiment, the invention provides a process for preparing acrylic oligomers prepared from $C_1$-$C_{20}$ alkyl and $C_5$-$C_{20}$ cycloalkyl (meth)acrylates, wherein said oligomers have a $M_n$ of about 300 g/mole to about 3,000 g/mole; a $M_w$ of about 700 g/mole to about 6,000 g/mole; and a $M_z$ of about 900 g/mole to about 10,000 g/mole. The Yellowness Index, according to ASTM E313 may be less than 2. In some embodiments, the process for forming at least partially hydrogenated oligomers may comprise the steps of polymerizing $C_1$-$C_{20}$ alkyl and $C_5$-$C_{20}$ cycloalkyl (meth)acrylates in the presence of a chain transfer agent and then contacting the resulting oligomers with an ion exchange resin before subjecting said oligomers to hydrogenation.

In another embodiment, the invention provides a process for hydrogenating the (meth)acrylic oligomers of the invention, which comprises contacting the (meth)acrylic oligomers of the invention, dissolved in a non-olefinic solvent, with hydrogen. The oligomers may be present in the solvent at a concentration of 10 to 60 wt % based on the total weight of oligomers and non-olefinic solvent. The oligomers may be contacted with hydrogen in the presence of a catalyst selected from (i) Group VIII metals with a support selected from metal oxides, carbon, carbide, nitride, or zeolite; or (ii) Raney Nickel; at a temperature of 50° to 200° C. and at a pressure of 50 to 1500 psig.

In some embodiments, the oligomers described herein can have a glass transition temperature ($T_g$) of at least about −100, at least about −75, at least about −50, at least about −25, at least about −10° C. and/or not more than about 20, not more than about 15, not more than about 10, not more than about 5, or not more than about 0° C., measured according to dynamic scanning calorimetry (DSC) as described in ASTM D7426-08(2013). The glass transition temperature of the oligomers can be in the range of from −100 to 20° C., from −100 to 0° C., from −50 to 10° C., or from −20 to 0° C.

In other embodiments, the oligomers described herein can have a $T_g$ of at least about 0, at least about 5, at least about 10, at least about 15, at least about 20, at least about 25, or at least about 30° C. and/or not more than about 150, not more than about 130, not more than about 120, not more than about 110, not more than about 100, not more than about 75, not more than about 60, not more than about 55, not more than about 50, not more than about 45, not more than about 40, not more than about 35° C., or it can be in the range of from about 0 to about 150° C., about 0 to about 120° C., about 5 to about 100° C., about 10 to about 60° C., about 15 to about 55° C., about 20 to 100° C., about 20 to about 50° C., about 25 to about 55° C., about 30 to about 50° C., about 5 to about 35° C., or about 10 to about 30° C.

The oligomers of the present invention may also have a Ring & Ball softening point of at least about 60, at least about 65, at least about 70, at least about 75, at least about 80, at least about 85, at least about 90, at least about 95, at least about 100, at least about 105, or at least about 110° C. and/or not more than about 130, not more than about 125, not more than about 120, not more than about 110, not more than about 105, not more than about 100, not more than about 95, not more than about 90, not more than about 85, or not more than about 80° C., measured according to ASTM D6493-99. The softening point of the oligomers can be in the range of from about 60 to about 130° C., about 65 to about 125° C., about 70 to about 120° C., about 90 to about 125° C., about 105 to about 125° C., about 60 to about 100° C., about 110 to about 120° C., about 60 to about 95° C., about 70 to about 90° C., about 80 to about 110° C., about 85 to about 105° C., about 90 to about 100° C., about 90 to about 120° C., about 95 to about 115° C., or about 100 to about 110° C.

When hydrogenated, the oligomers of the present invention may be more stable than similar but unhydrogenated compounds. For example, in some cases, the enhanced stability of the inventive oligomers may be evidenced by a higher than expected degradation temperature, measured by thermogravimetric analysis (TGA) according to ASTM E2250-11. In some embodiments, the temperature at which 10% weight loss of the oligomer backbone is achieved can be at least about 275, at least about 280, at least about 285, at least about 290, at least about 295, at least about 300, at least about 305, or at least about 310° C. and/or not more than about 350, not more than about 345, not more than about 340, not more than about 335, not more than about 330, not more than about 325, not more than about 320, not more than about 315, or not more than about 310° C. In some cases, the temperature at which 10% weight loss of the oligomer is achieved can be in the range of from about 275° C. to about 350° C., about 275° C. to about 330° C., about 275° C. to about 320° C., about 285° C. to about 315° C., or about 300 to about 330° C.

Additionally, when hydrogenated, the oligomers of the present invention may include little, or no, unsaturation, particularly with respect to the end groups. In some embodiments, the oligomers may have a residual olefin content of less than 3.5, not more than about 3.25, not more than about 3.0, not more than about 2.75, not more than about 2.5, not more than about 2.25, not more than about 2.0, not more than about 1.75, not more than about 1.5, not more than about 1.25, not more than about 1.0, not more than about 0.75, not more than about 0.5, not more than about 0.45, not more than about 0.40, not more than about 0.35, not more than about 0.30, not more than about 0.25, not more than about 0.20, or not more than about 0.15 weight percent, measured by $^1$H NMR.

The oligomers of the present invention can be used in a wide variety of end use compositions and applications. For example, the oligomers of the invention are useful as tackifiers in adhesive compositions, and, in particular, pressure sensitive adhesives. These materials could also be utilized in UV curable acrylic systems. The oligomers of the present invention are also useful in sealants and other elastomeric compositions. These materials are also useful in general polymer modification as plasticizers, leveling agents, viscosity reducers (rheology modifiers), and for increasing solids content in solvent-borne applications of all types with little detrimental impact on viscosity. Such end uses are referred to herein collectively as "compositions". In embodiments where the oligomers are used in the latter compositions, the $T_g$ of the oligomer may be in the range of from −100° C. to 0° C.

In one embodiment, the invention provides a composition comprising polymers or copolymers prepared from monomers selected from the group consisting of styrene, butadiene, acrylonitrile, ethylene, vinyl acetate, acrylic acid, esters of acrylic acid, methacrylic acid and esters of methacrylic acid or combinations thereof; and acrylic oligomers as described herein that are prepared from $C_1$-$C_{20}$ alkyl and $C_5$-$C_{10}$ cycloalkyl (meth)acrylates, wherein said oligomers have a $M_n$ of about 300 g/mole to about 3,000 g/mole; a $M_w$ of about 700 g/mole to about 6,000 g/mole; a $M_z$ of about 900 g/mole to about 10,000 g/mole; and wherein the Yellowness Index, according to ASTM E313 is less than 2.

In some embodiments, such a composition may be an adhesive composition such as, for example, a pressure sensitive adhesive (PSA) composition. Pressure sensitive adhesives (PSA) are viscoelastic materials that display both a fluid like character that is important for forming excellent mechanical contact with a surface under light pressure for a short amount of time, and an elastic solid character that resists various applied stresses after bond formation. The Handbook of Pressure Sensitive Adhesive Technology defines PSA and, in particular, their ability to wet surfaces (tack) as a modulus controlled process. Specifically PSA are described as being below a specific modulus of less than $10^5$ dyne/cm² at room temperature and that these materials displayed the ability to spontaneously (or with light pressure and low contact times) fully wet out an adherend. (Satas, D. Ed. *Handbook of Pressure Sensitive Adhesive Technology 3rd Edition*; Satas and Associates: R.I. 1999).

In some embodiments, a pressure sensitive adhesive can be prepared by combining at least one (meth)acrylic polymer or co-polymer with at least one oligomer as described herein. The resulting adhesive composition may include the (meth)acrylic polymer or co-polymer in an amount of at least about 40, at least about 45, at least about 50, at least about 55, at least about 60, or at least about 65 weight percent and/or not more than about 95, not more than about 90, not more than about 85, not more than about 80, not more than about 75, or not more than about 70 weight percent, based on the total weight of the adhesive composition, or it may be present in an amount in the range of from about 40 to about 90 weight percent, about 50 to about 90 weight percent, about 55 to about 85 weight percent, or about 60 to about 75 weight percent. Examples of (meth) acrylic polymers or co-polymers can include, but are not limited to, polymers and co-polymers formed from at least one monomer selected from the group consisting of acrylic acid, esters of acrylic acid, methacrylic acid, esters of methacrylic acid, and combinations thereof. Specific examples can include, but are not limited to, 2-ethylhexyl acrylate, butyl acrylate, acrylic acid, and combinations thereof.

In some embodiments, the (meth)acrylic polymer or co-polymer used to form the adhesive composition may be cross-linkable. This may be achieved by, for example, further polymerizing one of the (meth)acrylic monomers listed above with one or more cross-linkable monomers including one or more of a carboxyl, hydroxyl, epoxy, alkoxysilane, and an acetoacetyl group and/or one or more UV-sensitive functional groups such as benzophenone. When used, the cross-linkable monomer may be present in the final (meth)acrylic co-polymer in an amount of at least about 0.1, at least about 0.5, at least about 1, or at least about 1.5 weight percent and/or not more than about 30, not more than about 25, not more than about 20, not more than about 15, or not more than about 10 weight percent, based on the total weight of the (meth)acrylic co-polymer. The amount of cross-linkable monomer may be in the range of from about 0.1 to about 30 weight percent, about 0.5 to about 20 weight percent, or about 1 to 10 weight percent, based on the total weight of the (meth)acrylic co-polymer.

In some embodiments, the final acrylic polymer or co-polymer may have a $T_g$ of at least about −70, at least about −65, at least about −60, at least about −55, at least about −50, at least about −45, at least about −40, at least about −35, at least about −30, or at least about −25° C. and/or not more than about 50, not more than about 45, not more than about 40, not more than about 35, not more than about 30, not more than about 25, not more than about 20, not more than about 15, not more than about 10, not more than about 5, not more than about 0, not more than about −5, not more than about −10, or not more than about −15° C., measured as described previously. The glass transition temperature of the (meth)acrylic polymer or co-polymer used to form an adhesive composition of the present invention can be in the range of from about −70° C. to about 50° C., about −70° C. to about 20° C., about −70° C. to about 5° C., or about −70° C. to about −10° C.

The oligomer may be present in the adhesive composition in an amount of at least about 5, at least about 10, at least about 15, at least about 20, at least about 25, or at least about 30 weight percent and/or not more than about 60, not more than about 55, not more than about 50, not more than about 45, not more than about 40 weight percent, based on the total weight of the adhesive composition. In some embodiments, the (meth)acrylic oligomers used in the adhesive compositions have been hydrogenated to reduce any residual unsaturated bonds as set forth above.

Additionally, the adhesive composition may optionally contain other additives such as those described in U.S. Pat. No. 6,657,011, incorporated herein by reference. Such adhesive compositions are useful in preparing articles of the invention wherein at least one surface of the article is coated with the adhesive composition. Accordingly, the adhesive compositions may also further include other additives known in the art, such as emulsifiers, pigments, fillers, curing agents, thickeners, humectants, wetting agents, defoamer(s), biocides, adhesion promoters, colorants, additional tackifiers, UV stabilizers, waxes, and antioxidants.

Further, in some embodiments, the adhesive composition may exclude one or more additives typically found in conventional compositions. For example, in some cases, adhesive compositions of the present invention may include not more than about 2, not more than about 1.5, not more than about 1, not more than about 0.5, not more than about 0.25, not more than about 0.1, or not more than about 0.05 weight percent of one or more additives including emulsifiers, pigments, fillers, curing agents, thickeners, humectants, wetting agents, defoamer(s), biocides, adhesion promoters, colorants, additional tackifiers, UV stabilizers, waxes, and antioxidants. In other embodiments, the adhesive composition may be free of one or more of these additional components.

For example, in some cases, the adhesive compositions of the present invention may not include conventional tackifiers such as, for example, rosins, terpene phenolics, polyterpene resins, C5 resins, C9 resins, C5/C9 resins, pure monomer resins, and aromatic monomer resins, combinations thereof, and partial or fully hydrogenated forms thereof.

Other examples of tackifiying resins that may be excluded from compositions of the present invention include, but are not limited to, polyterpene resins, hydrogenated polyterpene resins, aliphatic petroleum hydrocarbon resins and hydrogenated derivatives thereof, aromatic hydrocarbon resins and hydrogenated derivatives thereof, alicyclic petroleum hydrocarbon resins and hydrogenated derivatives thereof. In some cases, adhesive composition of the present invention may include not more than about 5, not more than about 3, not more than about 2, not more than about 1, not more than about 0.5, or not more than about 0.1 weight percent of one or more or all of the above components, based on the total weight of the adhesive composition.

When the adhesive composition includes an (meth)acrylic co-polymer including cross-linkable functional groups as listed above, the composition may further include at least one cross-linking agent. Examples of suitable cross-linking agents can include, but are not limited to, metal chelates, aziridines, isocyanates, melamines, multifunctional (meth)acrylates having at least 2, at least 3, at least 4, or 5 or more functional groups, which can be matched with the appropriate functional group of the acrylic co-polymer. When used, the cross-linker may be present in the adhesive composition in an amount of at least about 0.01, at least about 0.05, at least about 0.075, at least about 0.10, or at least about 0.15 weight percent and/or not more than about 8, not more than about 5, not more than about 3, not more than about 2, not more than about 1, or not more than about 0.5 weight percent, based on the total weight of the composition.

Alternatively, the adhesive composition may be cross-linked without the use of a functionalized (meth)acrylic co-polymer or cross-linking agents by, for example, use of electron beam curing of the adhesive composition. In some embodiments, there may be substantially no, or no, cross-linking agent, such that the total amount of cross-linking agent is less than 0.01, less than 0.005, or less than 0.001 weight percent, based on the total weight of the adhesive composition.

In some embodiments, the adhesive composition may include one or more multi-functional acrylate cross-linking agents. Such cross-linking agents may be used when, for example, the adhesive composition is curable by radiation such as UV or thermal radiation. Examples of such cross-linking agents can include, but are not limited to, di(meth)acrylates, tri(meth)acrylates, and tetra(meth)acrylates such as 1,6-hexanediol di(meth)acrylate, poly(ethylene glycol) di(meth)acrylates, ethylene glycol diacrylate, 1,2-dodecanediol diacrylate, trimethylolpropane triacrylate, pentaerythritol tetracrylate, polybutadiene di(meth)acrylate, polyurethane di(meth)acrylates, and propoxylated glycerin tri(meth)acrylate, and mixtures thereof.

The specific type and amount of the multifunctional (meth)acrylate cross-linking agent may depend, at least in part, on the type and use of the adhesive composition. In some embodiments, when used, adhesive compositions as described herein may include at least one multi-functional (meth)acrylate in an amount of at least about 0.01, at least about 0.05, at least about 0.10, at least about 0.2, at least about 0.5, at least about 1, at least about 2, at least about 3, or at least about 5 parts by weight and/or not more than about 20, not more than about 18, not more than about 15, not more than about 12, not more than about 10, not more than about 8, not more than about 6, not more than about 5, not more than about 3 parts by weight, based on the adhesive composition taken as 100 parts by weight.

Additionally, in some embodiments, the adhesive composition may include at least one photoinitiator, which may or may not also function as a photocrosslinker. Examples of these types of additives can include, but are not limited to, chromophore substituted bistrichloromethyl triazines like 2,4-bis(trichloromethyl)-6-(4-methoxyphenyl)-s-triazine, 2,4-bis(trichloromethyl)-6-(3,4-dimethoxyphenyl)-s-triazine, 2,4-bis(trichloromethyl)-6-(I-napthyl)-s-triazine, 2,4-bis(trichloromethyl)-6-(2-napthyl)-s-triazine, and 2,4-bis(trichloromethyl)-6-(I-(4-methoxynapthyl))-s-triazine, and combinations thereof. When present, the photoinititiator may be present in an amount of at least about 0.01, at least about 0.05, at least about 0.10, at least about 0.2, at least about 0.5, at least about 1, at least about 2, at least about 3, or at least about 5 parts by weight and/or not more than about 20, not more than about 18, not more than about 15, not more than about 12, not more than about 10, not more than about 8, not more than about 6, not more than about 5, not more than about 3 parts by weight, based on the adhesive composition taken as 100 parts by weight.

Adhesive compositions and, in particular, pressure sensitive adhesive compositions formed according to embodiments of the present invention exhibit unexpected properties compared to conventional PSAs. In general, pressure sensitive adhesives exhibit a trade-off between adhesion/tack and shear strength/shear adhesion failure temperature (SAFT) and, overall, it is desirable to maximize both with minimal changes to either over time. Use of conventional tackifying resins, such as rosins or hydrocarbon-based tackifiers, in PSA compositions improve adhesion and tack, but lower shear and SAFT. Further, most conventional tackifying resins are less resistant to aging under a variety of conditions, particularly conditions of high heat and/or humidity. It has been discovered that use of the oligomers of the present invention as tackifying resins in acrylic pressure sensitive adhesives provides adhesive compositions with both enhanced adhesion, tack, and shear both initially and over time, even upon exposure to harsh environmental conditions.

In one embodiment, the invention provides a pressure sensitive adhesive composition comprising an (meth)acrylic polymer or co-polymer and oligomers as described herein that has a shear adhesion failure temperature (SAFT), measured according to PSTC-17, of at least about 150, at least about 155, at least about 160, at least about 165, at least about 170, at least about 175, at least about 180, at least about 185, at least about 190, or at least about 195° C. Alternatively, or in addition, the SAFT of the pressure sensitive adhesive can be not more than about 210, not more than about 205, not more than about 200, not more than about 195° C.

The pressure sensitive adhesive composition that includes inventive oligomers as tackifying resins may also exhibit a shear strength, measured according to PSTC-107 at ¼ in$^2$/kg, of at least about 50, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950 min. Additionally, or in the alternative, the pressure sensitive adhesive may exhibit a shear strength of not more than about 1200, not more than about 1150, not more than about 1100, not more than about 1050, not more than about 1000, or not more than about 975 min.

Pressure sensitive adhesives including oligomers of the present invention may also exhibit enhanced adhesion, as evidenced by increased peel strength. For example, in some embodiments, such pressure sensitive adhesives may exhibit a 180° peel strength on stainless steel, measured according to PSTC-101 of at least about 7, at least about 7.5, at least about 7.75, at least about 8, at least about 8.1, at least about 8.2, at least about 8.3 pounds per inch (lb/in) and/or not more than about 10, not more than about 9.5, not more than about 9, or not more than about 8.75 lb/in. Additionally, or in the alternative, these pressure sensitive adhesive compositions may exhibit a 180° peel strength on high density polyethylene (HDPE) of at least about 1.5, at least about 2, at least about 2.5, at least about 3, at least about 3.1, at least about 3.2, at least about 3.3, at least about 3.4, at least about 3.5 lb/in.

Further, in some embodiments, pressure sensitive adhesives employing an oligomer as described herein may also exhibit a rolling ball tack, measured according to PSTC-6, at least about 4, at least about 4.5, at least about 5, at least about 5.5, at least about 6, at least about 6.5, or at least about 7 mm and/or not more than about 28, not more than about 25, not more than about 22, not more than about 20, not more than about 18, not more than about 15, not more than about 12, not more than about 10, or not more than about 8 mm.

Pressure sensitive adhesives formulated with oligomers of the present invention retain desirable properties even after exposure to high heat and humidity for prolonged periods of time. In some embodiments, after exposure to heat and humidity as described in PSTC-9, aged pressure sensitive adhesives including oligomers of the present invention may exhibit a 180° peel strength on stainless steel, after aging, that is within about 12, within about 10, within about 8, within about 6, within about 5, within about 4, within about 3, or within about 2 percent of the 180° peel strength on stainless steel exhibited by the same composition prior to aging. As used herein, the term "within" means higher or lower than a given value. In some embodiments, the 180° peel strength on stainless steel after aging can be at least about 7, at least about 7.2, at least about 7.5, at least about 7.7, or at least about 8 lb/in.

Similarly, pressure sensitive adhesive compositions formulated with oligomers of the present invention may exhibit a 180° peel strength on HDPE, after aging, that is within about 27, within about 25, within about 22, within about 20, within about 18, within about 16, within about 14, within about 12, or within about 10 percent of the 180° peel strength on HDPE of the pressure sensitive adhesive prior to aging. In some embodiments, the 180° peel strength on HDPE after aging can be at least about 2.5, at least about 2.6, at least about 2.7, at least about 2.8, at least about 2.9, at least about 3.0, at least about 3.1, or at least about 3.2 lb/in.

In some embodiments, pressure sensitive adhesives utilizing oligomers of the present invention as tackifiers may exhibit properties falling in one or more, or all, of the above ranges. For example, pressure sensitive adhesives as described herein may have a 180° peel strength on stainless steel of at least 7 lb/in, a 180° peel strength on HDPE of at least 2 lb/in, a shear of at least 100 minutes, and a SAFT of at least 150° C. Such compositions may also exhibit a 180° peel strength on stainless steel after aging that is within about 10 percent of the 180° peel strength on stainless steel prior to aging and/or a 180° peel strength on HDPE after aging that is within 30 percent of the 180° peel strength on HDPE prior to aging.

Adhesive compositions, including pressure sensitive adhesive compositions, formulated with oligomers of the present invention may be prepared according to any suitable method. In some cases, the components of the adhesive composition may be blended, optionally with a solvent, to form a mixture, which can then be cast and dried onto a backing or other substrate to form an adhesive article. In other embodiments, the acrylic polymer or co-polymer, oligomer, and any optional additives may be blended to form a 100 percent solids mixture, which can be applied to the surface of a substrate and cured thermally or via UV radiation to form the finished adhesive article.

Adhesive articles of the invention may be various substrates such as solid laminates or composite substrates, films, tapes, and the like. Such substrates may be flexible, sheet-like materials such as, for example a sheet of paper, a polymer film, a textile fabric or nonwoven fiber sheet. The corresponding article may then take the form of, for example, an adhesive label or a pressure sensitive adhesive film or tape. In such articles, at least one surface of the article is coated with the adhesive composition of the invention. Such articles may be prepared by applying a coating of the adhesive composition to at least one surface of the article and allowing the composition to dry, thereby providing an adhesive layer consisting of the solids portion of the adhesive composition covering a portion of the surface of the substrate. Examples of methods of application of the composition to an article include roll coating, wire-wound rod coating, slot die coating, gravure coating, knife coating, hot melt coating, or curtain coating, followed by drying. The adhesive composition may be applied as either a continuous or discontinuous coating. Examples of such articles include pressure sensitive tapes, such as those described in U.S. Pat. Nos. 4,223,067; 2,925,174; 2,963,387; 5,439,748; 5,851,663; and 3,445,263, incorporated herein by reference.

In addition to being used as tackifier resins in adhesive compositions, the oligomers of the present invention may also be included as a functional additive in for other types of polymer compositions. For example, in some embodiments, oligomers of the present invention may be employed as an additive in a coating composition. The coating composition may be an aqueous coating composition, a solvent-based coating composition, or a powder coating composition and the oligomer may be present in an amount of at least about 1, at least about 2, at least about 4, at least about 6, at least about 8, at least about 10, at least about 15, or at least about 20 weight percent and/or not more than about 20, not more than about 15, not more than about 10, not more than about 8, not more than about 6, not more than about 4, not more than about 2, or not more than about 1, based on the total weight of the coating composition.

In some cases, the coating composition may be a liquid coating composition, applied to a surface and permitted to dry, while, in other embodiments, the coating composition may be at or near 100 percent solids. The oligomers of the present invention may function as leveling agents, flow aides, plasticizers, or tackifiers in such compositions. Examples of such coating compositions are described in WO9201748 and EP0801661, incorporated by reference herein.

When used in such applications, the oligomers of the present invention may be co-polymerized with other monomers to impart certain functionalities depending on the specific application. In some cases, use of low molecular weight, low polydispersity oligomers of the present invention may provide higher solids at lower viscosity, which may be advantageous for many applications. Further, hydrogenated oligomers are more stable when exposed to various types of energy, including, for example, UV and thermal energy and, as a result, such oligomers may be advantageously used in applications requiring exposure to such energy.

Additionally, oligomers of the present invention may be used as modifiers in thermoplastic elastomer (TPE) compositions. Thermoplastic elastomers are materials obtained by blending elastomers and plastics. The resulting compositions exhibit a unique combination of elastic properties, mechanical properties, and processability. The properties of such TPE compositions can be improved by including oligomers of the present invention as functional additives. Examples of TPE compositions suitable for use with the inventive oligomers are described in WO2009/009071, incorporated herein by reference.

This invention can be further illustrated by the following examples of several embodiments thereof. Although it will be understood that these examples are included merely for purposes of illustration and are not intended to limit the scope of the invention.

EXAMPLES

Preparation of a Cobalt Complex

A cobalt complex was prepared according to the following procedure. First, 10.00 grams (40 mmol) of Co(OAc)$_2$-4H$_2$O and 9.50 grams (80 mmol) of 2,3-dihydroxyiminobutane were weighed into a small beaker using an analytical balance. Next, the solids were combined and rinsed with about 600 mL of diethyl ether in a 2-L ¾-neck round-bottom flask. The flask was secured in a hood and equipped with an overhead stirrer. The mixture was then gentle stirred using the stirrer while it was sparged with nitrogen for 10 minutes. After 10 minutes, the nitrogen flow was reduced to a lower flow rate, but not stopped. Then, approximately 50 mL of BF$_3$-Et$_2$O was added to the mixture and allowed to stir all day with the lower-flow nitrogen. After about 8 hours, the nitrogen flow was stopped and the resulting mixture was permitted to stir overnight, after which the reaction medium was filtered to collect the brownish-colored solid precipitate. The precipitate was then washed once with about 100 mL of diethyl ether, followed by about 300 mL of distilled ice water. The resulting washed solids were then dried in a dessicator to provide the final cobaloxime. The cobaloxime was used in subsequent polymerizations to form various types of oligomers as described in the following Examples.

Preparation of a Comparative Tackifier

A comparative oligomer was prepared by introducing 60.0 grams of xylene and 90.0 grams of 2-methylbutanol into a 1000 ml glass reactor equipped with a heating jacket, agitator, reflux condenser, feed vessels and nitrogen gas inlet. The resulting mixture was then agitated and heated to reflux temperature of approximately 100° C. In a separate feed vessel 150.0 g of tert-butyl methacrylate, 1.5 g of n-dodecyl mercaptan, and 7.5 g of lauroyl peroxide were mixed and then fed to the reactor over a period of 3 hours. During the monomer feed the reaction mixture was maintained at a reflux temperature ranging from 105-110° C. After the feed was complete the reaction mixture was held for 30 minutes at reflux temperature of approximately 105° C. An initiator solution was prepared using 1.0 g of lauroyl peroxide dissolved in 60.0 g of toluene and 10.0 g of 2-methylbutanol and after the 30 minute hold was fed to the reactor over a period of approximately 20 minutes. The reaction was held at a reflux temperature of approximately 105° C. for 30 minutes and then cooled and discharged from the reactor. A solids content of 41.5% was measured indicating greater than 99% conversion of monomer to polymer.

Example 1

Into a 1500 ml glass reactor, equipped with a heating jacket, agitator, reflux condenser, feed vessels and nitrogen gas inlet, was charged 800 g tertiary-butyl methacrylate. Next, 160 mg of cobaloxime catalyst prepared as described above was dissolved in 20 g of ethyl acetate, filtered and the liquid was added to the reactor. Next, 130 g of ethyl acetate and 50 g of acetone were also charged to the reactor, agitation was started, and the total mixture was heated to reflux conditions at approximately 85° C. An initiator solution was prepared consisting of 0.8 g of 2,2'-azobis(isobutyronitrile) (AIBN) dissolved in 30 g of ethyl acetate and added to the reactor over approximately 20 minutes. The reaction mixture was held at approximately 80-87° C. for approximately 2 hours and another initiator solution consisting of 0.8 g of AIBN and 30.0 g of ethyl acetate was added over approximately 20 minutes.

The reaction was maintained at approximately 80-85° C. for an additional 2 hours and another initiator solution of 1.6 g of lauroyl peroxide dissolved in 90.0 g of ethyl acetate was added. The reaction was maintained at approximately 76-82° C. for an additional 1 hour at which point it was cooled down and discharged from the reactor as a solution. The liquid had a light yellow color presumably from residual catalyst. The solids content was measured to be 65.0% indicating a degree of monomer conversion to polymer of >99%. The molecular weight of the product was measured by GPC in THF against polystyrene standards. The resulting oligomer had a $M_n$ of 694 g/mole, a $M_w$ of 977 g/mole, and a $M_z$ of 1463 g/mole. Approximately 10 g of Amberlyst 36 was added to the finished polymer and mixed overnight. The resulting oligomer was colorless by observation.

Examples 2 Through 28

Several additional disclosed oligomers were prepared in a similar manner as described above in Example 1. The only differences between the procedure for preparing the disclosed oligomers in Examples 2-28, and the procedure for preparing the disclosed oligomer in Example 1 was the concentration of the cobaloxime (ppm by weight of monomer) and/or the starting monomer composition. Example 11 was synthesized from a different lot of catalyst that had increased activity, resulting in less catalyst needed to obtain desired $M_z$.

The molecular weight and polydispersity index for each of the oligomers prepared in Examples 2-28 were measured and the results are summarized in Table 2, below. Additionally, the ring and ball softening point was measured for several of the oligomers prepared in Examples 2-28 and these values are also provided in Table 2. Samples of the oligomers prepared in Examples 2-10 were combined with a pressure sensitive adhesive (PSA 1) described in Examples 29-39, below.

TABLE 2

Properties of Various (Meth)acrylate Oligomers

| Example | Monomers Type(s) | Monomers Amount(s), wt % | Chain Transfer Agent Type | Chain Transfer Agent Amount, ppm | $M_n$, g/mol | $M_w$, g/mol | $M_z$, g/mol | PDI | R & B Softening Point, °C. | Tg, °C. (High) | Tg, °C. (DSC $2^{nd}$ Heat) |
|---|---|---|---|---|---|---|---|---|---|---|---|
| Comparative | tBMA | 100 | nDDM | 10,000 | 5734 | 13569 | 20167 | 2.37 | nd | nd | 88.4 |
| 1 | tBMA | 100 | CoBF$_3$ | 200 | 694 | 977 | 1463 | 1.41 | nd | nd | nd |
| 2 | tBMA | 100 | CoBF$_3$ | 100 | 716 | 1027 | 1405 | 1.43 | 71.5 | 105 | 29.4 |
| 3 | tBMA | 100 | CoBF$_3$ | 50 | 1241 | 2204 | 3456 | 1.78 | 110.1 | 105 | 49.1 |
| 4 | tBMA | 100 | CoBF$_3$ | 25 | 2144 | 4840 | 7672 | 2.26 | 139.4 | 105 | 71.8 |
| 5 | IBOMA | 100 | CoBF$_3$ | 100 | 630 | 1059 | 1752 | 1.68 | 72 | 170 | 38.5 |
| 6 | IBOMA | 100 | CoBF$_3$ | 50 | 981 | 2456 | 4706 | 2.5 | 106.4 | 170 | 66.5 |
| 7 | IBOMA | 100 | CoBF$_3$ | 25 | 1396 | 4526 | 8920 | 3.24 | 147.4 | 170 | 93.4 |
| 8 | MMA | 100 | CoBF$_3$ | 100 | 676 | 1134 | 1658 | 1.68 | 70.5 | 105 | nd |
| 9 | MMA | 100 | CoBF$_3$ | 50 | 1043 | 1906 | 2909 | 1.83 | 115 | 105 | nd |
| 10 | MMA | 100 | CoBF$_3$ | 25 | 2857 | 5515 | 8402 | 1.93 | 116 | 105 | nd |
| 11 | tBMA | 100 | CoBF$_3$ | 20 | 1427 | 2439 | 4007 | 1.71 | nd | nd | nd |
| 12 | iBMA | 100 | CoBF$_3$ | 20 | 1755 | 3631 | 6959 | 2.07 | 66 | nd | nd |
| 13 | iBMA | 100 | CoBF$_3$ | 15 | 2203 | 4583 | 8099 | 2.08 | 85 | nd | nd |
| 14 | iBMA | 100 | CoBF$_3$ | 10 | 3068 | 6491 | 10,783 | 2.12 | 105 | nd | nd |
| 15 | BzMA | 100 | CoBF$_3$ | 25 | 1629 | 5687 | 13,381 | 3.49 | nd | nd | nd |
| 16 | BzMA | 100 | CoBF$_3$ | 12.5 | 3881 | 20,317 | 47,435 | 5.23 | nd | nd | nd |
| 17 | BzMA/MMA/HBA | 45/45/10 | CoBF$_3$ | 50 | 1343 | 2694 | 4382 | 2.01 | nd | nd | nd |
| 18 | BzMA/MMA/HBA | 40/40/20 | CoBF$_3$ | 50 | 3483 | 6736 | 10,038 | 1.93 | nd | nd | nd |
| 19 | BzMA/MMA/HBA | 40/40/20 | CoBF$_3$ | 25 | 4512 | 8630 | 13,520 | 1.91 | nd | nd | nd |
| 20 | CHMA | 100 | CoBF$_3$ | 50 | 1587 | 26875 | 85,960 | 16.93 | nd | nd | nd |
| 21 | CHMA | 100 | CoBF$_3$ | 25 | 2812 | 52,551 | 122,988 | 18.69 | nd | nd | nd |
| 22 | EHMA/BMA | 35/75 | CoBF$_3$ | 100 | 675 | 1125 | 1402 | 1.67 | nd | nd | nd |
| 23 | EHMA/BMA | 35/75 | CoBF$_3$ | 25 | 1042 | 1857 | 3650 | 1.78 | liquid | nd | nd |
| 24 | EPhEMA/MMA/MAA | 45/45/10 | CoBF$_3$ | 50 | 1479 | 2697 | 43,164 | 1.82 | nd | nd | nd |
| 25 | MMA/IBMA | 50/50 | CoBF$_3$ | 25 | 1305 | 2643 | 4782 | 2.02 | 103.5 | nd | nd |
| 26 | MMA/iBMA | 25/75 | CoBF$_3$ | 50 | 1291 | 2418 | 4484 | 1.87 | nd | nd | nd |
| 27 | MMA/iBMA | 25/75 | CoBF$_3$ | 25 | 1243 | 2272 | 3729 | 1.83 | nd | nd | nd |
| 28 | EPhEMA/MMA/HBA | 40/40/20 | CoBF$_3$ | 25 | 4426 | 8519 | 13,314 | 1.92 | nd | nd | nd |

Note:
"nd" = not determined

Examples 29 Through 39

A model solution acrylic pressure sensitive adhesive composition (PSA 1) was prepared by charging 55.0 g of ethyl acetate, 82.3 g of 2-ethylhexyl acrylate, and 4.33 g of acrylic acid into a 1000 ml glass reactor equipped with a heating jacket, agitator, reflux condenser, feed vessels and nitrogen gas inlet. The resulting mixture was then agitated and heated to a reflux temperature of approximately 80° C. An initiator solution was prepared by dissolving 0.17 g of lauroyl peroxide in 5.0 g of toluene and it was charged to the reactor. In a separate feed vessel, 247.0 g of 2-ethylhexyl acrylate, 13.0 g of acrylic acid, 260 g of ethyl acetate, and 0.17 g of lauroyl peroxide were mixed and fed to the reactor over a period of 2 hours while the temperature was maintained at a reflux temperature of approximately 80° C. After the feed the reaction was held at reflux temperature of approximately 80° C. In a separate feed vessel, 0.7 g of lauroyl peroxide is dissolved in 70.0 g of butyl acetate and was fed to the reactor over a period of 30 minutes. The reaction was held at a reflux temperature of 80-85° C. for an additional 60 minutes. Next, 50 g of butyl acetate was added as a diluent and the finished material was cooled and discharged. A solids content of 41.7% was measured indicating >99% conversion of monomer to polymer.

A cross-linker solution was prepared by dissolving 20 g of aluminum acetoacetonate in 20 g of 2,4-pentanedione and 160 g of toluene. For Examples 30 through 39, blends of the model acrylic PSA were formed with the disclosed tackifiers prepared in Examples 2-10 and the comparative tackifier. Each blend included 70% acrylic PSA (dry weight) and 30% tackifier (dry weight). All of the blends were crosslinked at 0.5% aluminum acetoacetonate (dry weight) based on acrylic PSA dry weight. Films of each blend were cast onto siliconized paper air dried for approximately ten minutes in a fume hood and then placed in a 150° C. forced air oven for 10 minutes. Dynamic mechanical analysis was performed on each of the films with a TA Instruments Ares RDA3 Rheometer in a parallel plate geometry and auto strain mode. The diameter of the plates was 8 mm and the gap was 1.704 mm. The frequency was 10 Hz and the heating rate was 6° C./min. The maximum strain was set at 5.0%.

Next, 180° peel tests were performed on the model PSA 1 (Example 29) as well as each of the PSA blends prepared in Examples 30 through 39 per the procedure described in PSTC-101. Other tests including the shear measurements per PSTC 107 (¼ in²/kg), shear adhesion failure temperature (SAFT) per PSTC-17, rolling ball tack per PSTC-6 and accelerated aging of PSA tapes per PSTC-9 were also performed for the model PSA 1 and each blend. The results are summarized in Table 3, below.

TABLE 3

Properties of Various Adhesive Compositions

| Example | Composition | | 180° Peel Test | | | | | SAFT | | Shear | |
| | PSA | Tackifier | 15 min | σ | 24 hour | σ | >72 h | σ | ° C. | σ | min | σ |
| --- | --- | --- | --- | --- | --- | --- | --- | --- | --- | --- | --- | --- |
| 29 | PSA 1 | None | 2.91 | 0.44 | 3.89 | 0.45 | 4.14 | 0.71 | 75.47 | 8.69 | 56.77 | 13.81 |
| 30 | PSA 1 | Comparative | 0.78 | 0.27 | 3.85 | 0.39 | 4.98 | 0.54 | 72.31 | 1.96 | 252.00 | 25.40 |
| 31 | PSA 1 | Example 2 | 5.63 | 0.43 | 6.43 | 0.21 | 6.96 | 0.68 | 68.20 | 1.48 | 127.23 | 47.25 |
| 32 | PSA 1 | Example 3 | 6.91 | 0.73 | 8.40 | 1.90 | 9.14 | 2.42 | 69.77 | 0.70 | 280.23 | 3.84 |
| 33 | PSA 1 | Example 4 | 5.25 | 0.63 | 7.29 | 0.66 | 7.77 | 0.20 | 75.50 | 8.41 | 687.20 | 101.12 |
| 34 | PSA 1 | Example 5 | 6.95 | 0.54 | 9.07 | 0.11 | 9.58 | 0.19 | 70.43 | 1.82 | 133.47 | 26.97 |
| 35 | PSA 1 | Example 6 | 6.26 | 0.34 | 8.52 | 1.70 | 7.91 | 1.45 | 89.00 | 1.70 | 471.90 | 202.77 |
| 36 | PSA 1 | Example 7 | 5.38 | 0.56 | 7.06 | 0.84 | 8.21 | 1.29 | 92.53 | 6.23 | 341.50 | 108.62 |
| 37 | PSA 1 | Example 8 | 2.71 | 0.11 | 3.13 | 0.75 | 3.40 | 0.32 | 50.77 | 2.76 | 61.30 | 32.79 |
| 38 | PSA 1 | Example 9 | nd | nd | nd | nd | nd | nd | nd | nd | nd | nd |
| 39 | PSA 1 | Example 10 | nd | nd | nd | nd | nd | nd | nd | nd | nd | nd |

Note:
"nd" = not determined

Referring now to FIG. 1, FIG. 1 provides a plot of storage modulus and tan δ as a function of temperature of the model PSA 1 (Example 29) and the model PSA 1 blended with the comparative tackifier (Example 30) and the model PSA 1 blended with the disclosed oligomer of Example 2 (Example 31) at 50% by weight solid polymer. In the storage modulus plot, the model PSA (Example 29) exhibits the lowest glass transition temperature and relatively flat plateau modulus between $1 \times 10^5$ and $1 \times 10^6$ dyn/cm$^2$. The model PSA 1 exhibits a peak tan δ of approximately −20° C.

As shown in FIG. 1, the rheology of the PSA composition is dramatically impacted by addition both the comparative tackifier and the tackifier prepared in Example 2, but there are substantial differences. For example, the higher molecular weight and higher $T_g$ comparative tackifier increases the $T_g$ of the resulting composition appreciably as seen in the storage modulus plot and in the peak tan δ value of −5° C. In addition to the $T_g$ increase, the comparative tackifier increases the plateau modulus by an order of magnitude and the tan δ plot displays a low peak tan δ value and comparable area under the curve at the $T_g$, indicating similar dissipative characteristics as the model PSA itself. Also, in the tan δ plot of the blend containing the comparative tackifier, there is a second peak at approximately 170° C., which is likely to be phase separated high molecular weight fractions of the poly(t-butyl methacrylate). The increase in glass transition temperature of the system is an expected and desirable effect for a tackifier, but the other desired effect or function of a tackifier is to lower plateau modulus, not increase it.

As shown in FIG. 1, the composition including the oligomer from Example 2 blended with PSA 1 displays a larger increase in $T_g$ as evidenced by a peak tan δ of approximately 8° C. The larger increase in $T_g$ exhibited by the blend of oligomer from Example 2 with the model PSA 1 composition is evidence of a greater degree of compatibility with the model PSA 1. Also, in contrast to the blend including the comparative tackifier, the blend including the oligomer from Example 2 lowers the plateau modulus by an order of magnitude and increases peak tan δ and area under the tan δ curve, indicating a more dissipative PSA which leads directly to improvement in adhesion.

Figure 2:
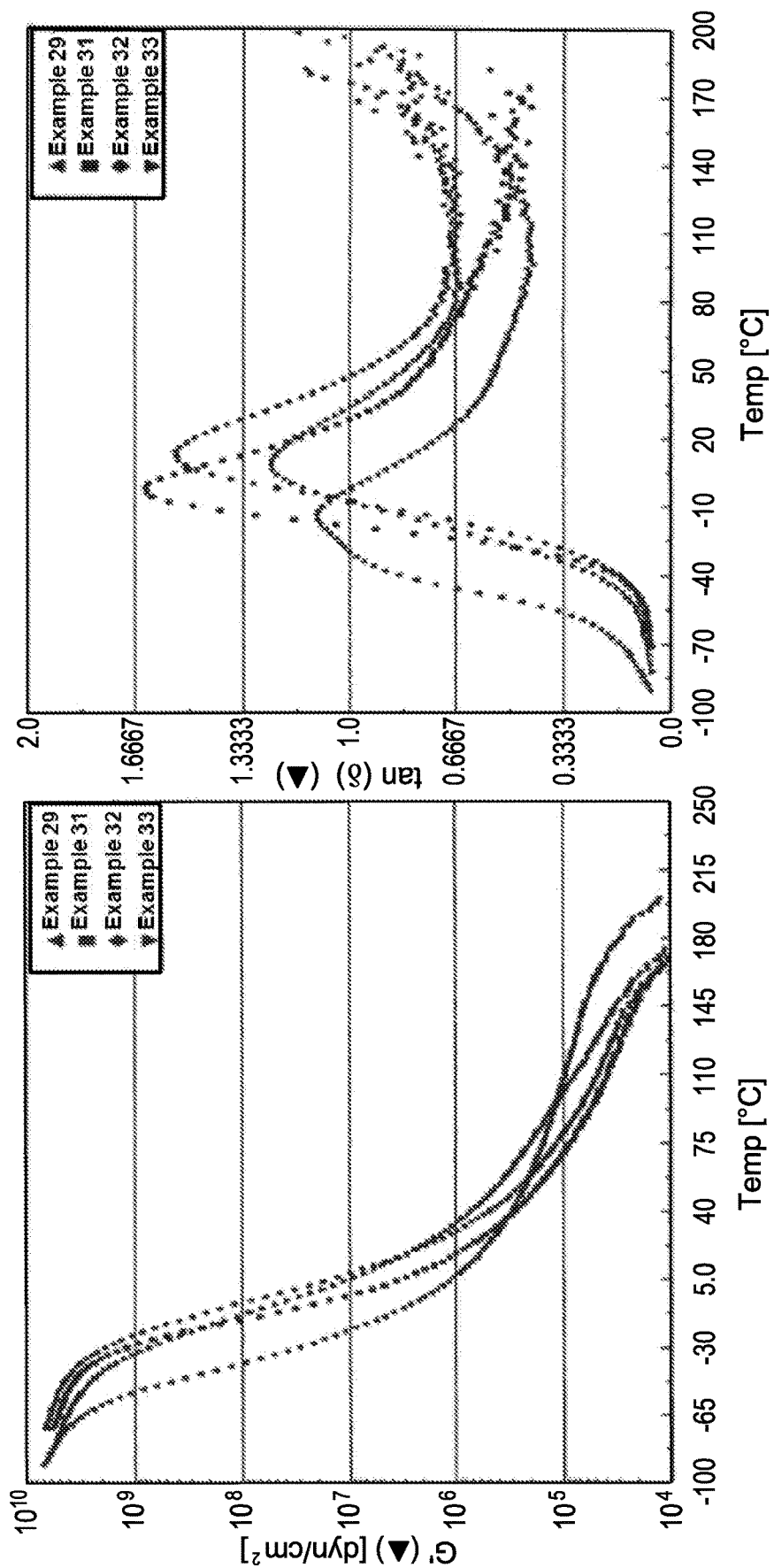
FIG. 2 is a plot of storage modulus and tan δ as a function of temperature of pressure sensitive adhesive blends including poly(t-butyl methacrylate) oligomers of varying molecular weights.

Turning now to FIG. 2, a plot of storage modulus and tan δ as a function of temperature of the model PSA 1 (Example 29) and blends of 70% model PSA 1 and 30% of the oligomers from Examples 2-4 (Examples 31-33), which are poly(t-butyl methacrylate) oligomers of varying molecular weight (and consequently $T_g$/softening point). The desirable tackifier behavior described previously of increased $T_g$, lower plateau modulus and greater dissipative character is observed in all three examples. However, as shown in FIG. 2, the blend including the highest molecular weight oligomer (Example 33) exhibits a plateaued effect, which may indicate an upper limit on molecular weight for this particular composition behaving as a tackifier.

Figure 3:
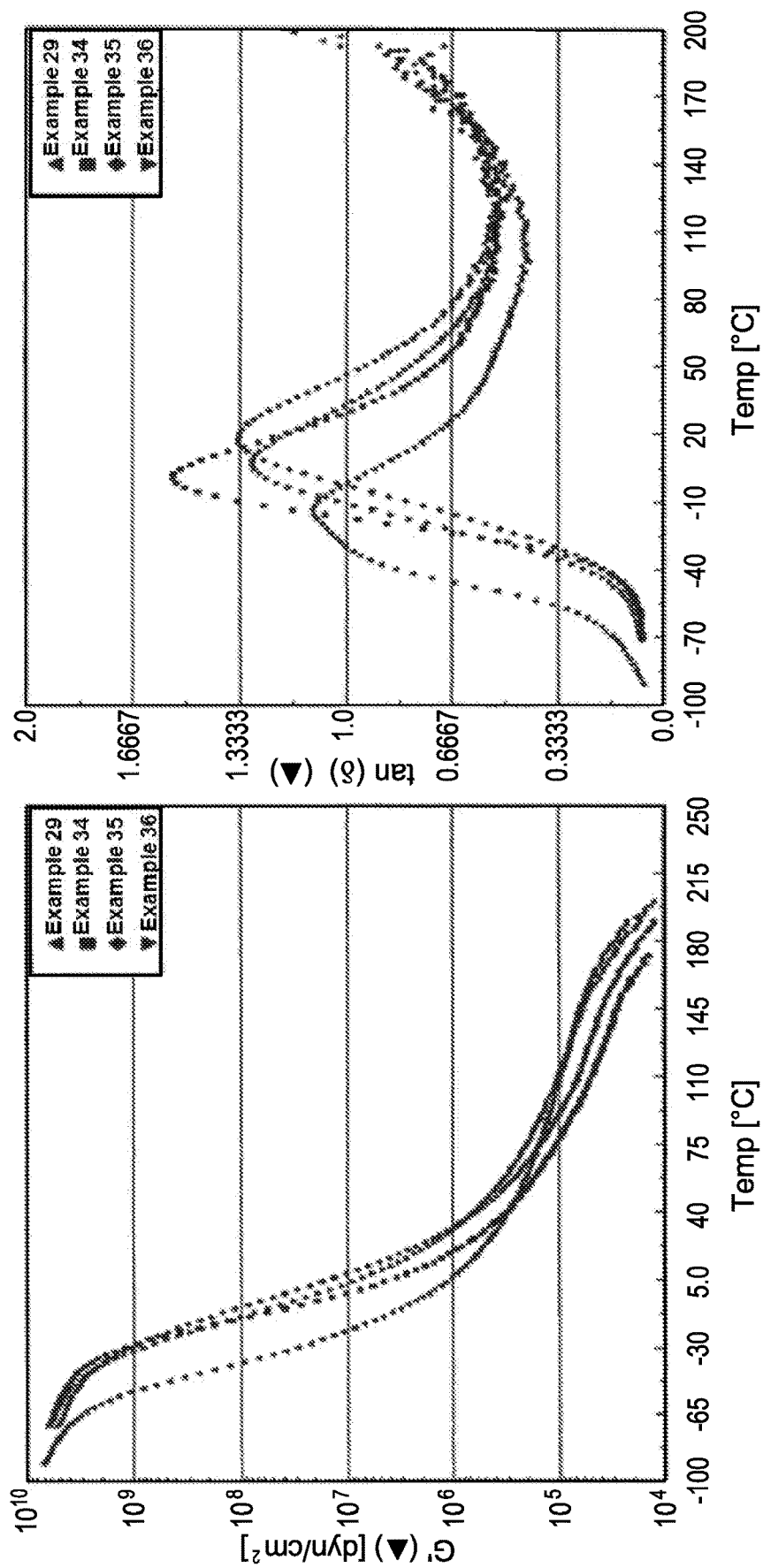
FIG. 3 is a plot of storage modulus and tan δ as a function of temperature of pressure sensitive adhesive blends including poly(isobornyl methacrylate) of varying molecular weights.
Figure 4:
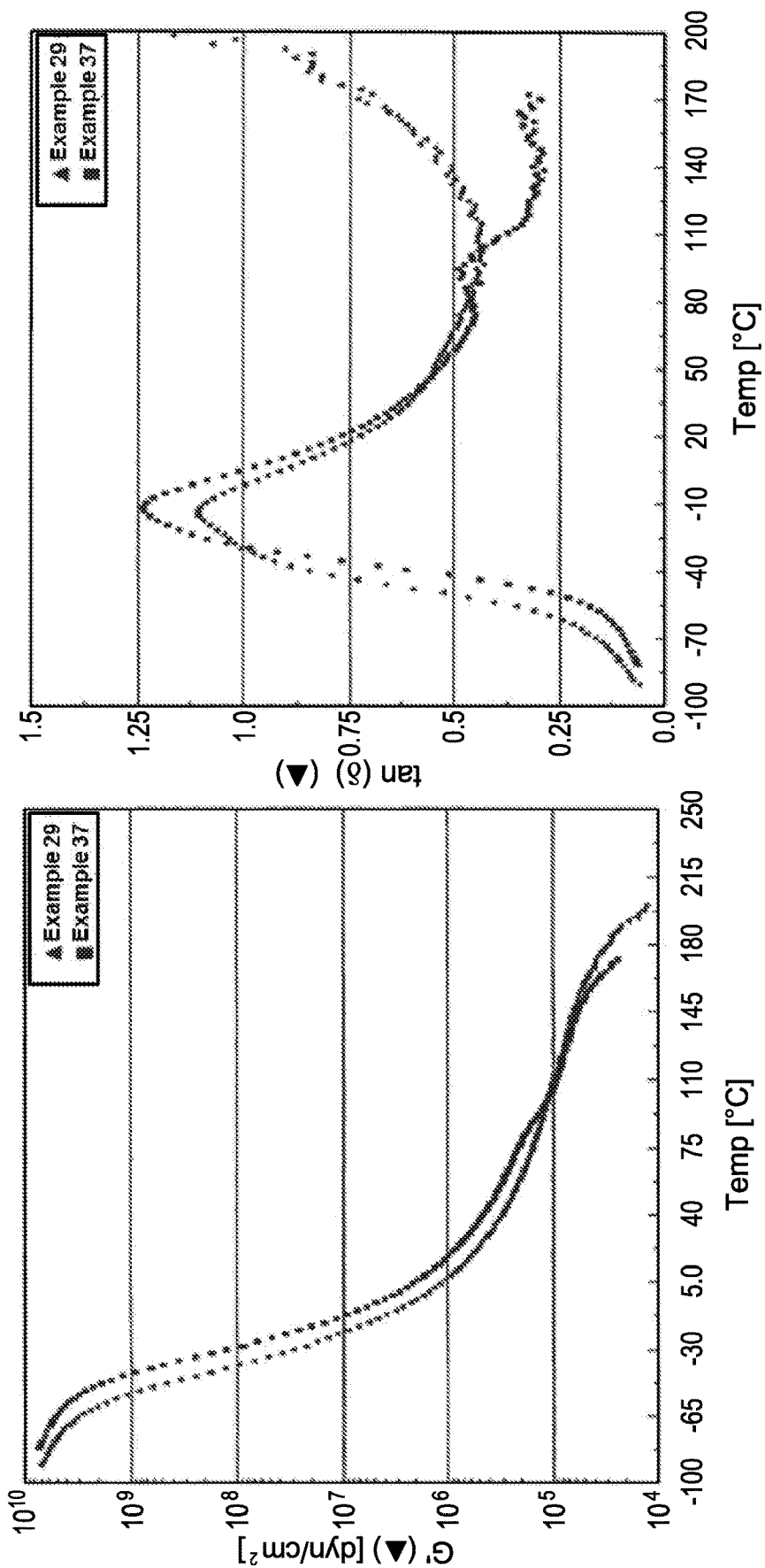
FIG. 4 is a plot of storage modulus and tan δ as a function of temperature of pressure sensitive adhesive blends poly (methyl methacrylate) of varying molecular weights.

Referring now to FIG. 3, a similar graph as provided in FIG. 2 is shown, but with the PSA blends including the oligomers from Examples 5-7 (Blends from Examples 34-36). These oligomers are (poly)isobornyl methacrylate oligomers of varying molecular weight (and $T_g$/softening point). Essentially the same behavior as Examples 2-4 is observed, further demonstrating the upper limit for molecular weight of these classes of materials. Similarly, FIG. 4 is the same type of plot as FIGS. 2 and 3, but illustrating the storage modulus and tan δ as a function of temperature of the model PSA blended with the oligomers from Examples 8-10 (blends in Examples 37-39), which are poly(methyl methacrylate) oligomers of varying molecular weight.

When blended with the model PSA 1, the higher molecular weight oligomers of Examples 9 and 10 resulted in PSA compositions that formed brittle films that were unable to be fabricated into samples suitable for rheological testing. Therefore, FIG. 4 shows only the behavior of the PSA composition including the lowest molecular weight MMA oligomer from Example 8 (blend in Example 37). The friable and opaque white appearance of the blends with the oligomers from Examples 9 and 10 are a very clear indication of incompatibility. As shown in FIG. 4, the storage modulus and tan δ plot for the PSA blend including the oligomer from Example 8 indicate very limited compatibility and tackification behavior because there is a minimal increase in $T_g$, no decrease in plateau modulus, no enhancement to the dissipative character of the blends, and the presence of a second $T_g$. Overall, these results demonstrate that there are compositional criticalities for an effective tackifier in addition to molecular weight.

Examples 40 Through 43

Another model solution acrylic pressure sensitive adhesive composition (PSA 2) was prepared by charging 74.53 g of ethyl acetate, 32.4 g of 2-ethylhexyl acrylate, 32.4 g of butyl acrylate and 3.41 g of acrylic acid into a 1500 ml glass reactor equipped with a heating jacket, agitator, reflux condenser, feed vessels and nitrogen gas inlet. The mixture was then agitated and heated to a reflux temperature of approximately 85° C. An initiator solution was prepared by dissolving 0.23 g of lauroyl peroxide in 5.0 g of ethyl acetate and was charged to the reactor. In a separate feed vessel, 183.6 g of 2-ethylhexyl acrylate, 19.3 g of acrylic acid, 439.7 g of ethyl acetate, and 0.23 g of lauroyl peroxide were mixed and fed to the reactor over a period of 3 hours while the temperature was maintained at a reflux temperature of approximately 80-85° C. After the feed the reaction was held at reflux temperature of approximately 80-85° C. In a separate feed vessel 0.91 g of lauroyl peroxide was dissolved in 70.0 g of ethyl acetate and was fed to the reactor over a period of 30 minutes. The reaction was held at a reflux temperature of 80-85° C. for an additional 60 minutes. Next, 100 g of toluene was added as a diluent and the finished material was cooled and discharged. A solids content of 42.0% was measured indicating >99% conversion of monomer to polymer.

A cross-linker solution was prepared by dissolving 20 g of aluminum acetoacetonate in 20 g of 2,4-pentanedione, and 160 g of toluene. Blends of the model acrylic PSA 2 were prepared with the disclosed oligomers of Examples 12-14 (Examples 41-43, respectively) employed as tackifiers. The blends included 60-90% of the acrylic PSA 2 (dry weight) and 10-40% tackifier (dry weight). All of the blends and the model PSA 2 (Example 40) were crosslinked at 0.5% aluminum acetoacetonate (dry weight) based on acrylic PSA dry weight. Films of the resulting tackified compositions were cast onto siliconized paper or 2 mil mylar film and air dried for approximately ten minutes in a fume hood and then placed in a 130° C. forced air oven for 10 minutes. Dynamic mechanical analysis was performed on the films with a TA Instruments Ares RDA3 Rheometer in a parallel plate geometry and auto strain mode. The diameter of the plates was 8 mm and the gap was 1.704 mm. The frequency was 10 Hz and the heating rate was 6° C./min. The maximum strain was set at 5.0%.

Figure 5:
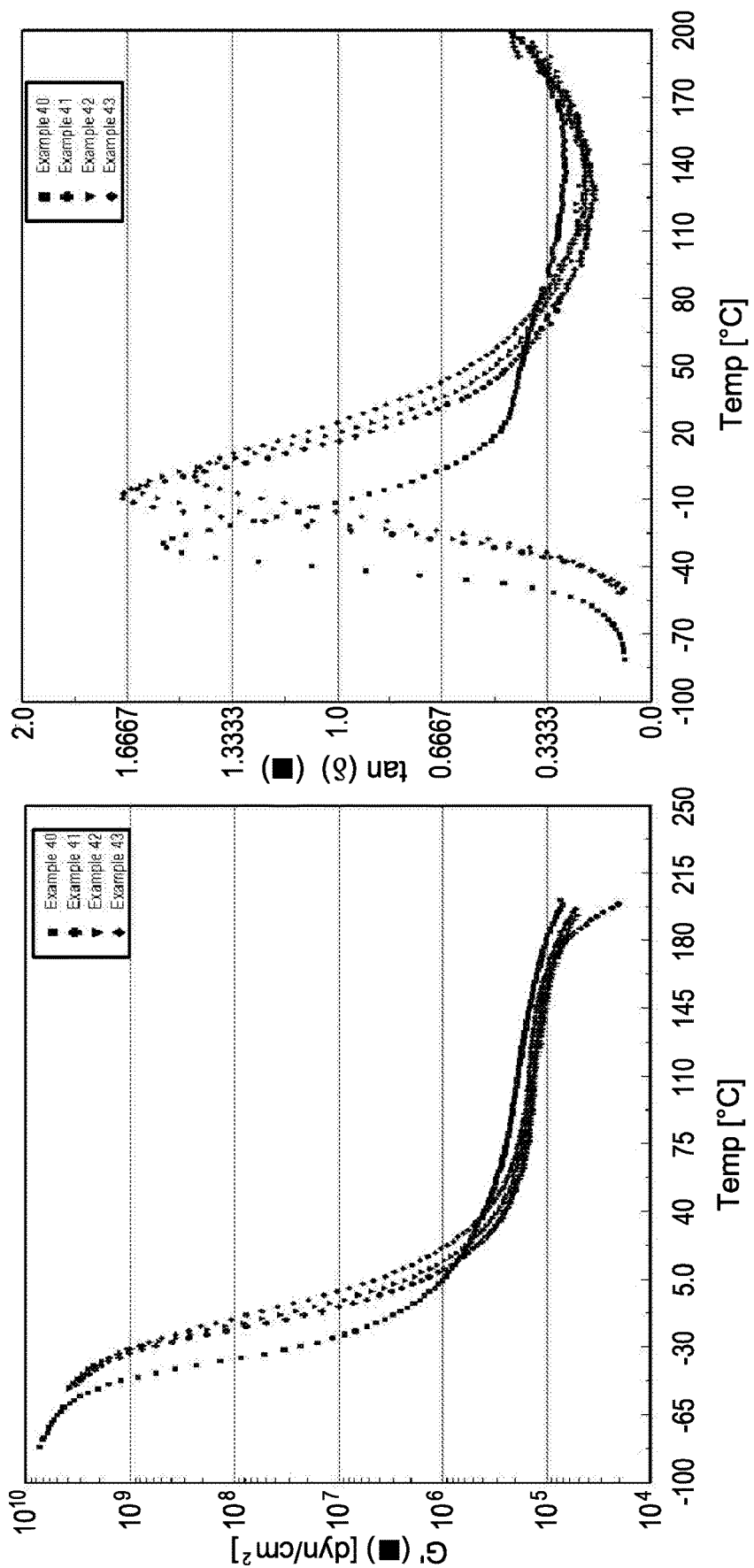
FIG. 5 is a plot of storage modulus and tan δ as a function of temperature of pressure sensitive blends of hydrogenated poly(iso-butyl methacrylate) oligomers of varying molecular weights.

Referring now to FIG. 5, a plot of storage modulus and tan δ as a function of temperature of the model PSA 2 (Example 40) and blends of 70% model PSA 2 and 30% of the oligomers from Examples 12-14 (Examples 41-43), which are poly(iso-butyl methacrylate) oligomers of varying molecular weight (and consequently $T_g$/softening point). Examples 41-43 increase the $T_g$ and lowers the plateau modulus as compared to neat PSA2 (Example 40), though in varying degrees. The blend with the highest $M_z$ oligomer (Example 43) demonstrates the largest increase in $T_g$ and the blend with the lowest $M_z$ oligomer (Example 41) demonstrates the lowest increase in $T_g$, which differs from FIGS. 2 and 3 in that the oligomers in those Figures appear to have an upper limit on molecular weight. This contradiction could be due to differences in the composition of the oligomer or the composition of the PSA. Additionally, Example 41 and Example 42 demonstrates an increase in dissipative character, marked by increased area under the tan δ curve; however, Example 43 shows a decrease.

Examples 44 Through 46

A methacrylate oligomer was prepared by introducing 800 grams of t-butyl methacrylate into a 1500-mL glass reactor equipped with a heating jacket, agitator, reflux condenser, feed vessels, and nitrogen gas inlet. Next, 32 mg of a cobaloxime chain transfer agent as described previously was dissolved in 20 grams of ethyl acetate and filtered, and the resulting liquid was added to the reaction vessel. The contents of the reaction vessel were agitated and the total mixture was heated to reflux conditions at a temperature of about 85° C. An initiator solution was prepared by combining 0.8 grams of 2,2'-azo-bis(isobutyronitrile) (AIBN) dissolved in 30 grams of ethyl acetate and the solution was added to the reaction vessel over approximately 20 minutes. The resulting mixture was stirred and held at a temperature between 80 and 87° C. for approximately 2 hours. Another initiator solution was formed from 0.8 grams of AIBN and 30 g of ethyl acetate and the resulting solution was added to the reactor over approximately 20 minutes.

The reaction was maintained at approximately 80-85° C. for an additional 2 hours and another initiator solution of 1.6 g of lauroyl peroxide dissolved in 90.0 g of ethyl acetate was added to the reactor. The reaction was maintained at approximately 76-82° C. for an additional 1 hour before being cooled down and discharged from the reactor as a solution. The liquid had a light yellow color and the solids content was measured to be 65.0%, which indicated a degree of monomer conversion to polymer of >99%. Next, approximately 40 grams of methanol and 5 5.ams sodium methoxide were added to the dissolved product to react with the polymerizable double bond yielded by the cobaloxime catalyst. This results in an oligomer with higher stability and renders the resulting oligomer inert to free-radical polymerization. The molecular weight of the stabilized oligomer was measured by GPC in THF against polystyrene standards and was as follows: a $M_n$ molecular weight of 752 g/mole, a $M_w$ molecular weight of 1025 g/mole, and a $M_z$ molecular weight of 1520 g/mole. Approximately 10 g of Amberlyst™ 36 (commercially available from Dow Chemical Company) was added to the finished polymer and mixed overnight. The resulting product appeared colorless upon visual observation.

A crosslinkable acrylic co-polymer (PSA 3) was prepared by introducing 74.53 grams of ethyl acetate, 32.4 grams of 2-ethylhexyl acrylate, 32.4 grams of butyl acrylate, and 3.41 grams of acrylic acid into a 1500 mL glass reactor equipped with a heating jacket, agitator, reflux condenser, feed vessels and nitrogen gas inlet. The resulting mixture was then agitated and heated to a reflux temperature of approximately 85° C. An initiator solution was prepared by dissolving 0.23 grams of lauroyl peroxide in 5.0 grams of ethyl acetate and was charged to the reactor. In a separate feed vessel, 183.6 grams of 2-ethylhexyl acrylate, 19.3 grams of acrylic acid, 439.7 grams of ethyl acetate, and 0.23 grams of lauroyl peroxide was mixed and fed to the reactor over a period of 3 hours while the temperature was maintained at a reflux temperature of approximately 80 to 85° C.

In a separate feed vessel, 0.91 grams of lauroyl peroxide was dissolved in 70 grams of ethyl acetate and was fed into a reactor over a period of 30 minutes. The reaction contents were held at a reflux temperature of 80 to 85° C. for an additional 60 minutes. Next, 100 grams of toluene was added as a diluent and the finished resin was cooled and recovered. The solids content of the reaction mixture was measured to be 42 percent, which indicated a greater than 99 percent conversion of monomer to acrylic co-polymer.

Next, a cross-linker solution was prepared by dissolving 20 grams of aluminum acetoacetonate in 20 grams of 2,4-pentanedione, and 160 grams of toluene. An example adhesive blend according to the present invention (Example 46) was formulated by combining 60 parts by weight (on a dry basis) of the acrylic co-polymer with 40 parts by weight (on a dry basis) of the methacrylate oligomer. A comparative adhesive blend (Example 45) was also formulated using 60 parts by weight (on a dry basis) of the acrylic co-polymer and 40 parts by weight (on a dry basis) of a hydrogenated rosin tackifier. Examples 44 through 46 were separately combined with 0.5 parts by weight (on a dry basis) of the cross-linking solution.

Films formed from each of the cross-linked compositions were cast onto siliconized paper or 2-mil Mylar film and air dried for approximately 10 minutes in a fume hood before being placed in a forced air oven at a temperature of 130° C. for 10 minutes. Dynamic mechanical analysis was performed on the resulting films with a TA Instruments Ares RDA3 Rheometer in a parallel plate geometry and auto strain mode. The diameter of the plates was 8 mm and the gap was 1.704 mm. The frequency was 10 Hz and the heating rate was 6° C./min.

Next, 180° peel adhesion tests on stainless steel, HDPE, and polycarbonate were performed samples of each adhesive composition as described in PSTC-101, and shear measurements were also taken at inch$^2$/kg according to PSTC-107. The shear adhesion failure temperature (SAFT) was measured for each composition according to PSTC-17, and the rolling ball tack was also determined according to PSTC-6. A sample of each composition was aged under conditions of high temperature and humidity as outlined in PSTC-9 and the 180° peel adhesion on stainless steel and HDPE were also determined for the aged samples. A percent change for the 180° peel adhesion values before and after aging on stainless steel and HDPE was calculated by dividing the difference between the peel adhesion before and after aging by the peel adhesion value before aging. The results of each of these analyses are summarized in Table 4, below.

relative olefin content, via $^1$H NMR, as well as the TGA at 10% total weight loss and yellowness index. All three tests were performed as described herein. The results are shown in Table 5, below. The difference seen in degradation between the various lots and the unhydrogenated control demonstrates increased stability of the tackifier backbone through the hydrogenation of the unsaturated end groups.

TABLE 5

Properties of Various Oligomers

| Lot | % Residual Olefin (by $^1$H NMR) | TGA (° C. at 10% total weight loss) | Yellowness Index |
| --- | --- | --- | --- |
| a | 0 | 305 | 0.56 |
| b | 0.3 | 310 | 0.69 |
| c | 0.4 | 298 | 0.74 |
| d | 0.1 | 306 | 1.02 |
| Control | 3.5 | 280 | 3.54 |

Hydrogenation of Lot a

The following is the procedure used for hydrogenating Lot a of the poly(t-butyl methacrylate) polymer shown in Table 5, above. First, 50 grams of 1% palladium supported on alumina (commercially available from BASF) was charged into a catalyst basket, which was then installed inside a 1.8-liter stainless steel reactor (commercially available from Parr). Then, 500 ml of isobutyl isobutyrate (commercially available from Eastman) was added to the auto-

TABLE 4

Properties of Several Adhesive Compositions

| Example | Composition PSA | Tackifier | Solids Content wt % | Shear min | SAFT ° C. | Tack mm | 180° Peel (Initial) SS, lb/in | 180° Peel (Initial) HDPE, lb/in | 180° Peel (Initial) PC, lb/in | 180° Peel (Aged) SS, lb/in | 180° Peel (Aged) HDPE, lb/in | 180° Peel (% Change) SS, lb/in | 180° Peel (% Change) HDPE, lb/in |
| --- | --- | --- | --- | --- | --- | --- | --- | --- | --- | --- | --- | --- | --- |
| 44 | PSA 3 | None | 42 | 26.2 | 180 | 9 | 4.54 | 1.1 | 4.9 | 4.5 | 1.35 | 0.9% | −22.7% |
| 45 | PSA 3 | Hydrogenated Rosin | 50 | 594.1 | 145 | 30 | 8 | 3.4 | 10.2 | 6.9 | 2.4 | 13.8% | 29.4% |
| 46 | PSA 3 | Oligomer | 52 | 955.3 | 195 | 7.2 | 8.3 | 3.5 | 9.9 | 8.2 | 3.2 | 1.2% | 8.6% |

As shown in Table 4, above, use of the inventive methacrylate oligomer in the adhesive composition enhances the peel strength, shear, SAFT and tack as compared to the untackified composition (Example 44). Additionally, for the same viscosity, Example 46 has a higher solids content than Example 45 and Example 44. Additionally, as shown in Table 4, use of the comparative hydrogenated rosin tackifier in Example 45 improves the peel, shear, and solids content, but has a negative effect on the SAFT. Further, the solids content of the comparative adhesive (Example 45) is higher than that of the untackified polymer composition (Example 44), but is less than the methacrylate oligomer adhesive composition (Example 46). Of the three compositions tested, the disclosed Example 46 exhibits the best performance after aging.

Example 47

Further evaluation was done using the disclosed oligomer prepared in Example 3. Several samples of this oligomer were hydrogenated in multiple lots using the procedures described in detail below. Samples from each iteration, labeled as lots a, b, c, and d, were tested to determine the clave. After leak check was performed with 500 psig helium, the autoclave was purged with 100 psig helium twice and then with 100 psig hydrogen once at ambient temperature, and finally vented to about 2 psig hydrogen. Then, the autoclave was heated to 100° C. and pressurized to 100 psig with hydrogen at 800 rpm agitation rate. After 1 hour catalyst activation, the autoclave was cooled down to ambient temperature and depressurized. Isobutyl isobutyrate (IBIB) was discharged from the autoclave. Then 30 g of the oligomer from Example 3 in approximately 390 g of ethyl acetate and 308 g of fresh IBIB were added into the autoclave, followed by leak check, helium and hydrogen purge steps as described above. Hydrogenation was carried out at 150° C., 500 psig hydrogen, and 800 rpm agitation rate. The final product was analyzed by proton NMR and the olefinic content was 0.0%, compared to 3.5% before hydrogenation.

Hydrogenation of Lot b

The following is the procedure used for hydrogenating Lot b of the poly(t-butyl methacrylate) polymer shown in Table 5, above. First, 1.96 grams of 1% palladium supported on alumina (commercially available from BASF) was charged into a catalyst basket, which was then installed inside a 100 ml stainless steel reactor (commercially available from Autoclave Engineers). Then, 60 g of isobutyl isobutyrate (commercially available from Eastman) was added to the autoclave. After leak check with 300 psig helium, the autoclave was purged with 100 psig helium twice and then with 100 psig hydrogen once at ambient temperature, and finally vented to about 2 psig hydrogen. Then, the autoclave was heated to 100° C. and pressurized to 100 psig with hydrogen at 800 rpm agitation rate. After 1 hour catalyst activation, the autoclave was cooled down to ambient temperature and depressurized. Isobutyl isobutyrate (IBIB) was discharged from the autoclave. Then a solution of 30 g of the oligomer from Example 3 in approximately 20 g of ethyl acetate and 40 g of fresh IBIB were added into the autoclave, followed by leak check, helium and hydrogen purge steps as described above. Hydrogenation was then carried out at 90° C., 150 psig hydrogen, and 800 rpm agitation rate. The final product was analyzed by proton NMR and the olefinic content was 0.3%, compared to 3.5% before hydrogenation.

Hydrogenation of Lot c

The following is the procedure used for hydrogenating Lot c of the poly(t-butyl methacrylate) polymer shown in Table 5, above. First, 1.7 grams of 1% palladium supported on alumina (commercially available from BASF) was charged into a catalyst basket, which was then installed inside a 100-ml stainless steel reactor (commercially available from Autoclave Engineers). Then, 60 g of isobutyl isobutyrate (commercially available from Eastman) was added to the autoclave. After leak check with 300 psig helium, the autoclave was purged with 100 psig helium twice and then with 100 psig hydrogen once at ambient temperature, and finally vented to about 2 psig hydrogen. Then, the autoclave was heated to 100° C. and pressurized to 100 psig with hydrogen at 800 rpm agitation rate. After 1 hour catalyst activation, the autoclave was cooled down to ambient temperature and depressurized. Isobutyl isobutyrate (IBIB) was discharged from the autoclave. Then a solution of 30 g of the oligomer from Example 3 approximately 20 g of ethyl acetate and 40 g of fresh IBIB were added into the autoclave, followed by leak check, helium and hydrogen purge steps as described above. Hydrogenation reaction was carried out at 120° C., 200 psig hydrogen, and 800 rpm agitation rate. The final product was analyzed by proton NMR and the olefinic content was 0.4%, compared to 3.5% before hydrogenation.

Hydrogenation of Lot d

The following is the procedure used for hydrogenating Lot d of the poly(t-butyl methacrylate) polymer shown in Table 5, above. First, 1.8 grams of 1% palladium supported on alumina (commercially available from BASF) was charged into a catalyst basket, which was then installed inside a 100 ml stainless steel reactor (commercially available from Autoclave Engineers). Then, 60 g of isobutyl isobutyrate (commercially available from Eastman) was added to the autoclave. After leak check with 300 psig helium, the autoclave was purged with 100 psig helium twice and then with 100 psig hydrogen once at ambient temperature, and finally vented to about 2 psig hydrogen. Then, the autoclave was heated to 100 C and pressurized to 100 psig with hydrogen at 800 rpm agitation rate. After 1 hour catalyst activation, the autoclave was cooled down to ambient temperature and depressurized. Isobutyl isobutyrate (IBIB) was discharged from the autoclave. Then a solution of 30 g of the disclosed oligomer from Example 3 in approximately 20 g of ethyl acetate and 40 g of fresh IBIB were added into the autoclave, followed by leak check, helium and hydrogen purge steps as described above. Then, the hydrogenation reaction was carried out at 150° C., 200 psig hydrogen, and 800 rpm agitation rate. The final product was analyzed by proton NMR and the olefinic content was 0.1%, compared to 3.5% before hydrogenation.

Examples 48 Through 51

Several UV syrups, with and without oligomers of the present invention as tackifying resins, were prepared as described herein. First, a sample of disclosed oligomer as described in Examples 11 above was hydrogenated in a similar manner as described in Example 47. Specifically, 500 g of activated palladium supported alumina (commercially available from BASF) was charged in to two catalyst baskets (250 g in each), which were then installed in a 5 gallon stainless steel reactor. Then 7500 g of a 50:50 ethyl acetate:poly(t-BMA) (Example 11) was added to the reactor. The reactor was sealed and purged (1) two times with nitrogen at about 100 psig and then (2) three times with $H_2$ at about 100 psig. Under about 200 psig ($H_2$), the temperature of the reactor was raised to 120° C. and the stirrer started (400 rpm). Once to temperature, the pressure of the reactor was increased to 1000 psig with $H_2$ and held for 4 hrs. At the completion of the hydrogenation, the reactor was allowed to cool to room temperature, the pressure released, and the contents collected. Several properties of the resulting hydrogenated poly(t-butyl methacrylate) oligomer (Example 48) was measured and the results are shown in Table 6, below, along with similar properties of the oligomer from Examples 11, which are reproduced from Table 2, above.

TABLE 6

Properties of Several Hydrogenated & Unhydrogenated Oligomers

| Example | Type | Chain Transfer Agent ppm | % Residual Olefin (by $^1$H NMR) | Oligomer Properties | | | | |
| --- | --- | --- | --- | --- | --- | --- | --- | --- |
| | | | | $M_n$, g/mol | $M_w$, g/mol | $M_z$, g/mol | PDI | R & B Softening Point, ° C. |
| 11 | Unhydrogenated | 20 | 1.1 | 1427 | 2439 | 4007 | 1.71 | 103 |
| 48 | Hydrogenated | 20 | 0.0 | 1427 | 2439 | 4007 | 1.71 | 103 |

First, a UV syrup including a polymer formed from 92.5 weight percent 2-ethylhexyl acrylate and 7.5 weight percent acrylic acid (92.5 2-EHA/7.5AA) was formed by charging 277.5 g 2-ethylhexyl acrylate, 22.5 g acrylic acid, and 3 g of a photoinitiator (commercially available as Darocur® 4265) into a 500 ml round bottom glass flask equipped with an agitator, reflux condenser, thermocouple and a nitrogen gas inlet. The mixture was sparged with nitrogen gas for 15 minutes while under agitation/mixing at ambient temperature (approximately 21° C.). The flask was then exposed to a UV 365-nm light source for approximately 7 minutes and was observed to thicken appreciably and the temperature increased to 35° C. At this point the UV source was extinguished and air was sparged into the mixture to stop the polymerization. The material was cooled and discharged to glass storage containers covered with black electrical tape to block all ambient light.

Next, a comparative UV composition (Example 49) was formed by adding 50 g of the UV Syrup in a small glass jar followed by 46.25 g of 2-ethylhexyl acrylate, 4.75 g of acrylic acid, 0.5 g of hexanediol diacrylate, and 0.5 g of Darocur® 4265. The jar was well mixed to ensure homogeneity. The resulting mixture was then was coated approximately 5 mils thick onto Performance Films T-10 siliconized PET release film. Another sheet of T-10 release film was placed on top of the coated adhesive and was then cured using an American Ultraviolet Co. air-cooled belt driven unit. The unit was outfitted with a medium pressure mercury lamp, the belt speed was set at 3 feet per minute (fpm), power setting was 300 W/in, and the measured intensity of UVa was 1.9 J/cm$^2$.

Next, a UV composition tackified with a non-hydrogenated oligomer (Example 50), as described in Example 11, was prepared by adding 35 g of UV Syrup to a small glass jar followed by 32.38 g of 2-ethylhexyl acrylate, 3.33 g of acrylic acid, 0.5 g of hexanediol diacrylate, 30 g of the disclosed non-hydrogenated oligomer from Example 11 and 0.5 g of Darocur® 4265. The jar was well mixed to ensure homogeneity. The resulting mixture was then coated approximately 5 mils thick onto a Performance Films T-10 siliconized PET release film. Another sheet of T-10 release film was placed on top of the coated adhesive and was then cured using an American Ultraviolet Co. air cooled belt driven unit. The unit was outfitted with a medium pressure mercury lamp, the belt was set at 3 feet per minute (fpm), power setting was 300 W/in, and the measured intensity of UVa was 1.9 J/cm$^2$.

Finally, another UV composition tackified with the hydrogenated oligomer described in Example 48 (Example 51) was prepared in a similar manner except 30 grams of the hydrogenated oligomer from Example 48 was included in the mixture rather than the non-hydrogenated Example 11 oligomer.

Figure 6:
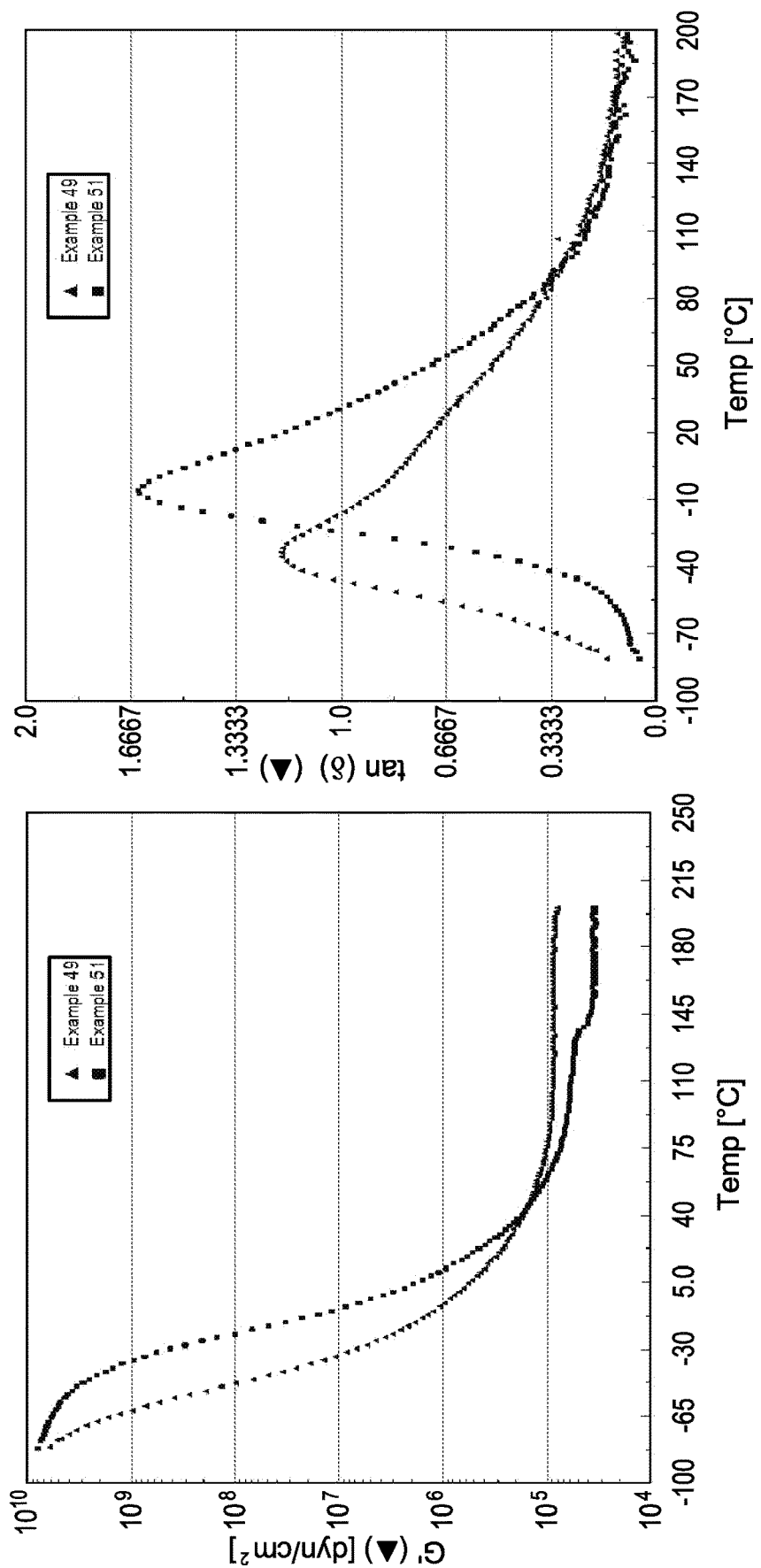
FIG. 6 is a plot of storage modulus and tan δ as a function of temperature of UV syrup blends of non-hydrogenated and hydrogenated poly(t-butyl methacrylate) and hydrogenated poly(i-butyl methacrylate).

Referring now to FIG. 6, FIG. 6 provides a plot of storage modulus and tan δ as a function of temperature of the comparative UV composition (Example 49) and UV composition tackified with the hydrogenated tackifier from Example 48 (Example 51). The UV composition tackified with the non-hydrogenated tackifier from Example 11 (Example 50) is not shown in FIG. 6, as it did not cure and was, therefore, unable to be evaluated. It is believed that the residual olefinic groups on the non-hydrogenated tackifier from Example 11 inhibited proper curing. Example 51, however, displays the desirable tackifier behavior described previously of increased $T_g$, lower plateau modulus and greater dissipative character, as compared to Example 49.

Example 52 Through 56

Kurarity LA-2140e, a thermoplastic elastomer commercially available from Kuraray America Inc., was weighed and added into a Brabender mixer equipped with a larger bowl attachment and processed at 200° C. until molten. Various oligomers previously described in Table 2 were weighed together and slowly added to the mixer at 200° C. Once all materials were added and torque readings stabilized, the blends (Examples 53-56), described below in Table 7, were left to mix 10 minutes and then were discharged.

All of the blends (Examples 53-56) and the Kurarity LA-2140e control (Example 52) were fabricated into plaques (5"×5"×⅛") by compression molding in a heated Carver press at 180° C. and approximately eight tons of pressure for five minutes. The films were then die cut into test articles for various physical tests including tear strength, tensile, or compression testing. Before die cutting, the plaques were tested for percent transmittance with a Gardner Haze-gard plus instrument.

Tensile samples were die-cut from these plaques and tested in accordance to ASTM D638 (Type V). The smaller "dog bones" were used due to the very flexible nature of the samples. As larger samples would have exceeded the elongation capacity of the group's Instron instrument. Tear samples were die cut to compliance with ASTM D624 (die C).

Melt flow rate was measured at 220° C. with a 1.1 kg weight. Densities were not measured or calculated for the individual blends so the melt flow rate results were reported in mL/10 min and are referred to as melt volume rate (MVR).

For compression set testing, ASTM D395-14 was used. Test specimens were conditioned to ambient lab temperature and humidity for 24 hours and then cut from 6-mm thick plaques using a punch style cutter with an inner diameter of 13 mm. Three samples of each plaque were loaded into a plate compression device with 4.5 mm spacer bars for constant deflection in accordance to test method B. Samples were then allowed to remain under constant ambient lab conditions or a 70° C. oven for 22 hours. Thickness measurements were taken before compression and 30 minutes after a lab conditioning phase after being removed from the devise. Calculations were done and results reported in accordance to ASTM 395-14. Hardness testing was done in accordance with ASTM D2240-05. Samples were measured from the same 6 mm plaques used for compression testing, but only before compression samples were cut. A type B shore A durometer was and a very dense lab bench was used as a base for testing. Measurements were collected and recorded in compliance with ASTM D2240-05. All properties determined from the previously described tests are listed below in Table 7.

TABLE 7

Properties of Several TPE Compositions

| Example | Composition TPE | Composition Tackifier | Tackifier % elongation at break | Tensile at break (psi) | 50% mod. (psi) | 300% mod. (psi) | Youngs mod. (psi) | Tear Strength (psi) | Comp. Set | 70° C. Comp. Set | Hard. Shore A | % Trans | MVR (CM³/ 10 min) |
|---|---|---|---|---|---|---|---|---|---|---|---|---|---|
| 52 | Kurarity LA-2140e | None | 2689 | 532 | 18 | 68 | 0.04 | 48 | 24.1 | 84.3 | 28 | 93.2 | 3.9 |
| 53 | Kurarity LA-2140e | Example 9 | 2650 | 419 | 122 | 227 | 0.31 | 123 | 67.4 | 92.1 | 62 | 92.8 | 18.1 |
| 54 | Kurarity LA-2140e | Example 13 | 2646 | 333 | 19 | 55 | 0.03 | 55 | 44.2 | 97.4 | 22 | 92.5 | 21.6 |
| 55 | Kurarity LA-2140e | Example 25 | 2737 | 335 | 15 | 38 | 0.02 | 30 | 21.8 | 87 | 16 | 93.4 | 9.4 |
| 56 | Kurarity LA-2140e | Ex 24/Ex 25 (50:50) | 2626 | 359 | 23 | 76 | 0.04 | 65 | 26.1 | 95 | 28 | 93.5 | 13.6 |

Referring to the properties in Table 7, Example 53 showed a marked increase in 50% modulus, 300% modulus, Young's Modulus, Tear Strength, Compression Set, 70° C. Compression Set, Shore Hardness, and MVR as compared to Example 52, the comparative Kurarity LA-2140e TPE. Examples 54-56 had properties similar to that of Example 52, with the Compression Set of Example 54 being the exception. The Compression Set of Example 54 increased compared to that of Example 52. Another notable difference is the improved ease of processability of blends with (meth) acrylate oligomer (Examples 53-56) as compared to the TPE (Example 52).

The invention has been described in detail with particular reference to preferred embodiments thereof, but it will be understood that variations and modifications can be effected within the spirit and scope of the invention.

We claim:

1. (Meth)acrylic oligomers prepared from $C_1$-$C_{20}$ alkyl and $C_5$-$C_{20}$ cycloalkyl (meth)acrylates, wherein said oligomers have a $M_n$ of from about 300 to about 3000 g/mole; a $M_z$ of from about 900 to 10,000 g/mole; wherein the Yellowness Index, according to ASTM E313 is less than 2; wherein said oligomers are hydrogenated to a residual olefin content, measured by $^1$H NMR, of less than 3.5 weight percent; wherein the $C_1$-$C_{20}$ alkyl and $C_5$-$C_{20}$ cycloalkyl is selected from the group consisting of cyclohexyl, methyl, t-butyl, isobutyl, norbornyl, dicyclopentadienyl, and isobornyl; and wherein the glass transition temperature of the oligomer is −100 to 120° C.

2. The oligomers of claim 1, wherein the $M_n$ is from about 700 to about 2500 g/mole.

3. The oligomers of claim 1, wherein the $M_z$ is from about 1400 to about 6000 g/mole.

4. The oligomers of claim 1, wherein the polydispersity ($M_w/M_n$) is less than 3.5.

5. The oligomers of claim 1, wherein the polydispersity ($M_w/M_n$) is less than 2.5.

6. The oligomers of claim 1, wherein the polydispersity ($M_w/M_n$) is less than 2.0.

7. The oligomers of claim 1, wherein the Ring & Ball softening point of the oligomers is in the range of from 65° C. to 125° C.

8. The oligomers of claim 1, wherein the $M_w$ is in the range of about 700 to about 6000 g/mole and the glass transition temperature of the oligomers is in the range of from 5 to 55° C.

9. (Meth)acrylic oligomers prepared from at least one type of monomer, wherein said monomer is selected from the group consisting of isobutyl (meth)acrylate, t-butyl (meth) acrylate, isobornyl (meth)acrylate, cyclohexyl (meth)acrylate, norbornyl (meth)acrylate, methyl (meth)acrylate, and combinations thereof, wherein said oligomers have a $M_n$ molecular weight of from about 300 to about 3000; a $M_z$ molecular weight of from about 900 to about 10,000; and a $M_w$ molecular weight of from about 700 to about 6000, wherein said oligomers are hydrogenated to a residual olefin content, measured by $^1$H NMR, of less than 3.5 weight percent; and wherein said oligomers have a Ring & Ball softening point in the range of from 60° C. to 125° C.

10. The oligomers of claim 9, wherein said oligomers have a glass transition temperature in the range of from about 5° C. to about 60° C.

11. The oligomers of claim 9, wherein the polydispersity (Mw/Mn) of the oligomer is less than 2.5.

12. The oligomers of claim 9, wherein said oligomers are hydrogenated to a residual olefin content, measured by $^1$H NMR, of less than 1.5 weight percent.

13. The oligomers of claim 9, wherein said oligomers have an Mz molecular weight of 2000 to 6000, a Ring and Ball softening point of 70° C. to 120° C., a glass transition temperature of from 10 to 55° C., and a Yellowness Index according to ASTM E313 of less than 2, and wherein according to TGA ASTM E2550-11 to record onset of degradation, the temperature at which 10% weight loss of the oligomer backbone is achieved is in the range of from about 300° C. to about 330° C.

14. A composition comprising the oligomers of claim 1.

15. An adhesive composition comprising the oligomers of claim 1.

16. The oligomers of claim 1, wherein said oligomers comprise more than 92 weight percent of residues of a single monomeric component comprising one of the $C_1$-$C_{20}$ alkyl or the $C_5$-$C_{20}$ cycloalkyl (meth)acrylates.

17. The oligomers of claim 9, wherein said oligomers comprise more than 92 weight percent of residues of a single monomeric component comprising a $C_1$-$C_{20}$ alkyl or a $C_5$-$C_{20}$ cycloalkyl (meth)acrylate.

* * * * *